US008759256B2

(12) United States Patent  
Parrish et al.

(10) Patent No.: US 8,759,256 B2
(45) Date of Patent: *Jun. 24, 2014

(54) HERBICIDE COMPOSITION COMPRISING HERBICIDE COMPOUND IN ACID FORM AND ACIDIFYING AGENT

(75) Inventors: Scott K. Parrish, Spokane, WA (US); Richard A. Beardmore, Windsor, CO (US); Anthony E. Herold, Greeley, CO (US)

(73) Assignee: Platte Chemical Company, Greeley, CO (US)

( * ) Notice: Subject to any disclaimer, the term of this patent is extended or adjusted under 35 U.S.C. 154(b) by 1136 days.

This patent is subject to a terminal disclaimer.

(21) Appl. No.: 12/701,279

(22) Filed: Feb. 5, 2010

(65) Prior Publication Data

US 2010/0184599 A1 Jul. 22, 2010

Related U.S. Application Data

(63) Continuation of application No. 11/098,829, filed on Apr. 4, 2005, now abandoned, which is a continuation of application No. 10/102,799, filed on Mar. 21, 2002, now Pat. No. 6,906,004.

(60) Provisional application No. 60/325,289, filed on Sep. 26, 2001, provisional application No. 60/325,342, filed on Sep. 26, 2001, provisional application No. 60/325,343, filed on Sep. 26, 2001, provisional application No. 60/361,016, filed on Feb. 28, 2002.

(51) Int. Cl.
*A01N 37/10* (2006.01)

(52) U.S. Cl.
USPC .......................................................... 504/324

(58) Field of Classification Search
CPC ................................ A01N 37/40; A01N 25/04
See application file for complete search history.

(56) References Cited

U.S. PATENT DOCUMENTS

| 3,755,339 A | 8/1973 | McKendry |
| 3,761,486 A | 9/1973 | McGregor |
| 3,937,826 A | 2/1976 | Harris |
| 4,188,487 A | 2/1980 | Los |
| 4,445,925 A | 5/1984 | Young |
| 4,816,060 A | 3/1989 | Steller et al. |
| 4,971,630 A | 11/1990 | Skaptason |
| 4,994,101 A | 2/1991 | Young |
| 5,078,782 A | 1/1992 | Nielsen et al. |
| 5,118,338 A | 6/1992 | Moller |
| 5,189,414 A | 2/1993 | Tawara |
| 5,221,319 A | 6/1993 | Van Haften et al. |
| 5,268,352 A | 12/1993 | Dexter |
| 5,270,286 A | 12/1993 | Ong |
| 5,280,008 A | 1/1994 | Cahoy et al. |
| 5,288,692 A | 2/1994 | Young |
| 5,317,042 A | 5/1994 | Narayanan |
| 5,328,889 A | 7/1994 | Van Haften et al. |
| 5,411,944 A | 5/1995 | Young |
| 5,416,067 A | 5/1995 | Van Haften et al. |
| 5,498,773 A | 3/1996 | Noveroske et al. |
| 5,538,936 A | 7/1996 | Hermansky |
| 5,538,938 A | 7/1996 | Duckworth |
| 5,558,806 A | 9/1996 | Policello et al. |
| 5,565,409 A | 10/1996 | Sato et al. |
| 5,668,085 A | 9/1997 | Forbes et al. |
| 5,696,024 A | 12/1997 | Szamosi et al. |
| 5,707,928 A | 1/1998 | Baker |
| 5,741,502 A | 4/1998 | Roberts |
| 5,877,112 A | 3/1999 | Roberts et al. |
| 5,994,271 A | 11/1999 | Ravetta et al. |
| 6,069,115 A | 5/2000 | Pallett et al. |
| 6,071,857 A | 6/2000 | Vogt et al. |
| 6,127,317 A | 10/2000 | De Carvalao Castro et al. |
| 6,156,705 A | 12/2000 | Mueninghoff |
| 6,165,939 A | 12/2000 | Agbaje et al. |
| 6,180,563 B1 | 1/2001 | Ruegg et al. |
| 6,180,566 B1 | 1/2001 | Nielsen et al. |
| 6,187,715 B1 | 2/2001 | Narayanan et al. |
| 6,207,617 B1 | 3/2001 | Gillespie |
| 6,232,272 B1 | 5/2001 | Roberts et al. |
| RE37,313 E | 8/2001 | Roberts |
| 6,369,001 B1 | 4/2002 | Jimoh |
| 6,541,424 B2 | 4/2003 | Roberts et al. |
| 6,703,346 B2 * | 3/2004 | Herold et al. ................. 504/128 |
| 6,803,345 B2 | 10/2004 | Herold et al. |
| 6,831,038 B2 | 12/2004 | Volgas et al. |
| 6,906,004 B2 * | 6/2005 | Parrish et al. ................. 504/127 |

(Continued)

FOREIGN PATENT DOCUMENTS

| AU | 2002-254345 | 4/2003 |
| AU | 2002-255869 | 6/2008 |

(Continued)

OTHER PUBLICATIONS

McMullan,Effect of adjuvant and acidifying agent on imazamethabenz efficacy, Can. J. Plant Sci. 72: 1389-92, Oct. 1992.*
Turner et al.,Complexing agents as herbicide additives, Weed Research, 1978, vol. 18, pp. 199-207.*
Report from the Food and Agriculture Organization of the United Nations entitled "FAO Specifications and Evaluations for Agricultural Pesticides, Picloram", Jul. 2005, 22 pages.
Briggs et al., "Physico-chemical Factors Affecting Uptake by Roots and Translocation to Shoots of Weak Acids in Barley," Pesticide Science, vol. 19, pp. 101-112 (1987).
Brown et al., Basis for Soybean Tolerance to Thifensulfuron Methyl, Agricultural Products Department, E.I. du Pont de Nemours & Co., Stine/Haskell Research Center, Newark, Delaware 19714, accepted May 11, 1990, pp. 303-313.

(Continued)

*Primary Examiner* — Alton Pryor
(74) *Attorney, Agent, or Firm* — Faegre Baker Daniels LLP

(57) ABSTRACT

Described are herbicide compositions and methods for their preparation and use, in particular, herbicide compositions and methods relating to herbicide compositions containing herbicide compounds in acid form, and further including an acidifying agent.

13 Claims, No Drawings

(56) References Cited

U.S. PATENT DOCUMENTS

| | | |
|---|---|---|
| 6,939,555 B2 | 9/2005 | Volgas et al. |
| 7,094,735 B2 * | 8/2006 | Herold et al. ............... 504/254 |
| 8,232,230 B2 | 7/2012 | Volgas et al. |
| 2001/0034304 A1 | 10/2001 | Volgas et al. |
| 2002/0039970 A1 | 4/2002 | Roberts et al. |
| 2002/0107149 A1 | 8/2002 | Volgas et al. |
| 2002/0108415 A1 | 8/2002 | Volgas et al. |
| 2002/0160916 A1 | 10/2002 | Volgas et al. |
| 2003/0144147 A1 | 7/2003 | Herold et al. |
| 2003/0153461 A1 | 8/2003 | Parrish et al. |
| 2003/0153462 A1 | 8/2003 | Herold et al. |
| 2004/0127364 A1 | 7/2004 | Herold et al. |
| 2004/0167032 A1 | 8/2004 | Volgas et al. |
| 2005/0026780 A1 | 2/2005 | Parrish |
| 2005/0137091 A1 | 6/2005 | Herold et al. |
| 2005/0170967 A1 | 8/2005 | Parrish et al. |
| 2006/0205601 A1 | 9/2006 | Herold et al. |

FOREIGN PATENT DOCUMENTS

| | | |
|---|---|---|
| CA | 1168465 A1 | 6/1984 |
| CA | 1 225 533 | 8/1987 |
| CA | 2 462 122 | 4/2003 |
| CA | 2 462 127 | 4/2003 |
| CA | 2462124 | 4/2003 |
| CA | 2462955 | 4/2003 |
| DE | 2 328 192 | 1/1974 |
| EP | 0 100 440 | 2/1984 |
| EP | 0 163 598 | 4/1985 |
| EP | 0 217 125 | 4/1987 |
| EP | 0 243 522 B1 | 9/1989 |
| EP | 0 334 041 | 9/1989 |
| EP | 0 357 553 | 3/1990 |
| EP | 0 433 577 | 6/1991 |
| EP | 0 454 968 | 11/1991 |
| EP | 0 216 126 | 4/1993 |
| EP | 0 641 161 | 10/1996 |
| EP | 0 512 739 | 11/1996 |
| EP | 0 645 083 | 2/1999 |
| EP | 0 703 724 | 2/2002 |
| EP | 1 432 316 | 6/2004 |
| EP | 1 432 311 | 7/2006 |
| EP | 1 432 314 | 5/2007 |
| EP | 1 432 307 | 9/2007 |
| GB | 2 230 955 | 11/1990 |
| GB | 2 267 825 | 12/1993 |
| JP | 62-242606 | 10/1987 |
| JP | 4-230607 | 8/1992 |
| JP | 2005-503419 | 2/2005 |
| JP | 2005-512963 | 5/2005 |
| WO | WO 92/13454 | 8/1992 |
| WO | WO 92/21686 | 12/1992 |
| WO | WO 94/19941 | 9/1994 |
| WO | WO 96/08150 | 3/1996 |
| WO | WO 98/17109 | 4/1998 |
| WO | WO 99/55155 | 11/1999 |
| WO | WO 00/42847 | 7/2000 |
| WO | WO 00/67571 | 11/2000 |
| WO | WO 01/52650 | 7/2001 |
| WO | WO 02/11536 | 2/2002 |
| WO | WO 02/063956 | 8/2002 |
| WO | WO 03/103396 | 12/2003 |

OTHER PUBLICATIONS

Brown et al., "Metabolic pathways and Residue Levels of Thifensulfuron methyl in Soybeans", J. Agric. Food Chem. 1993:41, pp. 1724-1730.

Brown, et al., "Mode of Action, Crop Selectivity, and Soil Relations of the Sulfonylurea Herbicides", Pestic. Sci. 29: 263-281 (1990).

Devine et al., Uptake and Accumulation of the Herbicides Chlorsulfuron and clopyralid in Excised Pea Root Tissue, Plant Physiol. (1987) 85, 82-86.

Forest Glossary of Terms—H, Copyright © 2001, Province of British Columbia, downloaded from www.gov.bc.ca, 6 pages.

"Glyphosate" from www.soils.wisc.edu/virtual_museum/glyphosate/glyphosate_tx.html; originally released Dec. 25, 1999, last modified Dec. 31, 2000.

Hay et al., "Chemistry of Sulfonylurea Herbicides", Pestic. Sci. 29:247-261 (1990).

International Search Report issued in PCT/US02/08787, mailed Sep. 19, 2002, 7 pages.

International Search Report issued in PCT/US02/08830, mailed Sep. 17, 2002, 6 pages.

International Search Report issued in PCT/US02/08952, mailed Dec. 5, 2002, 12 pages.

International Search Report issued in PCT/US02/08953, mailed Dec. 17, 2002, 12 pages.

Knowles, D.A., "Chemistry and Technology of Agrochemical Formulations", Springer-Verlag, copyright 1998, pp. 147-157.

McMullan, "Effect of adjuvant and acidifying agent on imazamethabenz efficacy," Chemical Abstracts, Can. J. Plant Sci., vol. 72, No. 4, pp. 1389-1392 (1992) CA 118 :209455.

Milton J. Rosen, "Surfactants and Interfacial Phenomena," John Wiley & Sons, pp. 239-240 (1978).

Moxness et al., Environment and spray additive effects on picloram absorption and translocation in leafy spurge (*Euphorbia esula*), Weed Science, 1989, 37(2):181-186.

Negre, M. et al., "Interaction of Imidazolinone Herbicides With Soil Humic Acids, Experimental Results and Molecular Modeling," *J. Environ. Sci. Health*, B36(2), 107-125 (2001).

Overbeek, et al., Microemulsions, pp. 111-132, published in Surfactants ISBN 0-12-682180-1.

PCT/US02/08952 Annex to Form PCT/ISA/206, Communication Relating to the Results of the Partial International Search, 4 pages.

PCT/US02/08953 Annex to Form PCT/ISA/206, Communication Relating to the Results of the Partial International Search, 3 pages.

Plaschke et al. (In situ AFM study of sorbed humic acid colloids at different pH, Colloids and Surfaces A: Physicochemical and Engineering Aspects, vol. 160, Issue 3, Dec. 1999, pp. 269-279).

Royneberg et al., "Cycloxydim absorption by suspension-cultured velvetleaf (*Abutilon theophrasti* Medic.) cells", Weed Research, 1994, vol. 34, 1-9.

Sherrick et al., "Effects of adjuvants and environment during plant development on glyphosate adsorption and translocation in field bindweed," Chemical Abstracts, Weed Sci., vol. 34, No. 6, pp. 811-816 (1986) CA 106 : 14601.

Shone et al., "Absorption and translocation of 2,4-dichlorophenoxyacetic acid (2,4-D) by barley roots," Chemical Abstracts, Annu. Rep.—Agric. Res. Counc., pp. 32-33 (1973) CA 85:57935.

Simon et al., "The Effect of pH on the Biological Activities of Weak Acids and Bases", New Phytologist 51(2), 1952, 163-190.

Tomlin, C., Ed., The Pesticide Manual, 14th Edition, p. 1026.

Tomlin, C., Ed., The Pesticide Manual, Tenth Edition, p. 1338, (1995).

Turner et al., "Complexing agents as herbicide additives," Chemical Abstracts, Weed Res., vol. 18, No. 4, pp. 199-207 (1978) CA 89 : 158688.

Wyrill, J.B. et al., "Glyphosate Toxicity to Common Milkweed and Hemp Dogbane as Influenced by Surfactants," Weed Science, vol. 25, No. 3 pp. 275-287 (May 1977).

Zsoldos et al., "Effects of ph changes on ion and 2,4-D uptake of wheat roots," Chemical Abstracts, Dep. Plant Physiol., pp. 77-80 (1978) CA 92:192532.

"Glyphosate" from www.soils.wisc.edu/virtual_museum/glyphosate/glyphosate_tx.html; originally released Dec. 25, 1999, last modifiedDec. 31, 2000.

Chemical Abstracts, McMullan, "Effect of adjuvant and acidifying agent on imazamethabenz efficacy," Can. J. Plant Sci., vol. 72, No. 4, pp. 1389-1392 (1992) CA 118 :209455.

Chemical Abstracts, Sherrick et al., "Effects of adjuvants and environment during plant development on glyphosate adsorption and translocation in field bindweed," Weed Sci., vol. 34, No. 6, pp. 811-816 (1986) CA 106 : 14601.

Chemical Abstracts, Shone et al., "Absorption and tranlocation of 2,4-dichlorophenoxyacetic acid (2,4-D) by barley roots," Annu. Rep.—Agric. Res. Counc., pp. 32-33 (1973) CA 85:57935.

(56) References Cited

OTHER PUBLICATIONS

Chemical Abstracts, Turner et al., "Complexing agents as herbicide additives," Weed Res., vol. 18, No. 4, pp. 199-207 (1978) CA 89 : 158688.
Chemical Abstracts, Zsoldos et al., "Effects of ph changes on ion and 2,4-D uptake of wheat roots," Dep. Plant Physiol., pp. 77-80 (1978) CA 92 : 192532.
Hay et al., "Chemistry of Sulfonylurea Herbidides", Pestic. Sci. 29:247-261 (1990).
International Search Report issued in PCT/US02/08787, mailed Sep. 17, 2002, 7 pages.
International Search Report issued in PCT/US02/08952, mailed May 12, 2002, 12 pages.
Partial International Report issued in PCT/US02/08952, mailed Oct. 24, 2002, 4 pages.
Partial International Search Report issued in PCT/US02/08953, mailed Oct. 24, 2002, 3 pages.
Search Report issued in Brazilian Application No. PI0212871-3, dated Dec. 5, 2011, 1 page.
Simon et al., "The Effect of pH on the Bilogical Activities of Weak Acids and Bases", New Phytologist 51(2), 1952, 163-190.
The Ministry of Forest of British Colombia, 2001, glossary H.
The Pesticide Manual, 14th Edition, Tomlin, p. 1026.

\* cited by examiner

HERBICIDE COMPOSITION COMPRISING HERBICIDE COMPOUND IN ACID FORM AND ACIDIFYING AGENT

This application is a Continuation application U.S. patent application Ser. No. 11/098,829, filed Apr. 4, 2005, which claims the benefit of U.S. patent application Ser. No. 10/102,799, filed Mar. 21, 2002, which claims the benefit of U.S. Provisional Application Ser. No. 60/325,289, U.S. Provisional Application Ser. No. 60/325,342, and U.S. Provisional Application Ser. No. 60/325,343, all filed Sep. 26, 2001, and the benefit of U.S. Provisional Application Ser. No. 60/361,016, filed Feb. 28, 2002.

FIELD OF THE INVENTION

The invention relates to herbicide compositions and their preparation and use, and in particular to herbicide compositions and methods relating to herbicide compositions containing herbicide compounds in acid form, and further including an acidifying agent.

BACKGROUND

Commercially available herbicide compositions include a very large variety of active herbicide compounds. Such herbicide compositions can be prepared from different types of precursor compositions, and can be commercially available and used in a variety of different types of compositions, including, for example, compositions referred to as wettable powders, water dispersible granules, granules, aqueous solutions, water soluble powders, emulsifiable concentrates, oil-based flowables, concentrated emulsions, suspo-emulsions, emulsions, suspensions, suspension concentrates, mixtures, dispersions, and microemulsions, as well as others. Any of these different types of compositions may have different advantages or disadvantages relating to factors such as the mode of application and the type of active ingredient included in the herbicide composition.

Examples of just a few available active herbicide compounds include those of the general class known as phenoxy herbicides, e.g., 2,4-dichlorophenoxyacetic acid (known as 2,4-D), MCPA acid, MCPP acid; those of the general class known as pyridine herbicides, (e.g., triclopyr, fluoroxypyr); those of the general class of benzoic acid herbicides, (e.g., dicamba acid); those of the general class of aryloxy phenoxy propionic acid herbicides, (e.g., fluazifop acid and quizolofop acid); water-insoluble diphenyl ether type herbicides (e.g., oxyfluorfen or acifluorfen); glyphosate compounds (N-(phosphonomethyl)glycine), e.g., in the acid form, referred to as glyphosate acid, or in a salt form such as the IPA salt form; imidizole herbicide compounds (e.g., imazapyr or imazaquin); as well as others. Often, salt and ester forms of herbicide compounds tend to be more soluble in water and are preferentially chosen for use over acid forms of herbicide compositions.

A specific class of sulfuric acid adduct is described in U.S. Pat. Nos. 4,445,925, 4,994,101, and 5,288,692, (to Young) as useful with certain herbicide compounds.

New forms of useful or improved herbicide compositions are always desirable, especially those that show advantages in processing, application, environmental profile (e.g., volatility), or efficacy.

SUMMARY OF THE INVENTION

The invention relates to herbicide compositions for controlling plant growth, wherein the herbicide composition includes a herbicide compound in acid form, and also further includes an acidifying agent. Preferably, the herbicide composition, as applied, has a pH that is below the pKa of the herbicide compound.

The herbicide composition can be prepared from precursor ingredients such as microemulsion-forming concentrates, microemulsions, suspension concentrates, or any other type or form of herbicide compositions or herbicide precursor composition or concentrate. Acidifying agent can be added to the herbicide composition at any stage of processing, preparation, or use. The herbicide compound in acid form can be any herbicide compound known to exist in an acid form. And the acidifying agent can be any acidifying agent capable of reducing the pH of the herbicide composition, preferably to an acidic pH and most preferably to a pH below the pKa of the herbicide compound.

While others such as Young have included sulfuric acid adducts in herbicide compositions with certain herbicide compounds, other acidifying agents have now been discovered to be useful and even provide benefits such as improved efficacy. Also, additional benefits can occur in particular upon applying a herbicide composition that includes a herbicide compound in the acid form as opposed to other forms such as ester forms or salt forms.

An aspect of the invention relates to a herbicide composition comprising a herbicide compound in acid form and an acidifying agent, wherein the herbicide compound in acid form is other than glyphosate acid.

Another aspect of the invention relates to a herbicide composition comprising a herbicide compound in acid form selected from the group consisting of: a phenoxy herbicide, a pyridine herbicide, a benzoic acid herbicide, a quinolinic acid herbicide, an aryloxy phenoxy propionic acid herbicide, and combinations thereof, and wherein the herbicide composition includes an acidifying agent.

Another aspect of the invention relates to a herbicide composition comprising a herbicide compound in acid form and an acidifying agent, wherein the acidifying agent is selected from the group consisting of: sulfuric acid, hydrochloric acid, nitric acid, acetic acid, phosphoric acid, perchloric acid, polyphosphoric acid, and combinations thereof, and the herbicide composition does not include an adduct of sulfuric acid and a compound of the formula:

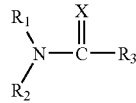

wherein X is chalcogen, and each of $R_1$, $R_2$, and $R_3$ is independently selected from hydrogen and organic radicals.

Another aspect of the invention relates to a herbicide composition comprising herbicide compound in acid form and an acidifying agent, wherein the acidifying agent is other than an acidifying agent selected from the group consisting of sulfuric acid; an adduct of sulfuric acid and a compound of the formula:

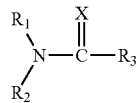

wherein X is chalcogen, and each of $R_1$, $R_2$, and $R_3$ is independently selected from hydrogen and organic radicals; and mixtures thereof.

Another aspect of the invention relates to a herbicide composition comprising a formulation selected from the group consisting of a microemulsion-forming-concentrate that contains a herbicide compound in acid form and a microemulsion that contains a herbicide compound in acid form, the herbicide composition comprising an acidifying agent.

Yet another aspect of the invention relates to a method of applying a herbicide composition. The method comprises preparing a herbicide composition comprising herbicide compound in acid form and acidifying agent, wherein the herbicide compound in acid form is other than glyphosate acid. The herbicide composition comprising the herbicide compound in acid form and acidifying agent is applied to control plant growth.

Another aspect of the invention relates to a method of applying a herbicide composition. The method comprises preparing a herbicide composition comprising herbicide compound in acid form and acidifying agent, wherein the herbicide compound in acid form selected from the group consisting of: a phenoxy herbicide, a pyridine herbicide, a benzoic acid herbicide, a quinolinic acid herbicide, an aryloxy phenoxy propionic acid herbicide, and combinations thereof. The herbicide composition comprising the herbicide compound in acid form and acidifying agent is applied to control plant growth.

DETAILED DESCRIPTION

Herbicide compositions of the invention include a herbicide compound in its acid form and an acidifying agent. The term "herbicide composition" refers to a composition that includes a herbicide compound, including (as will be described in more detail below) microemulsion-forming concentrates or microemulsions, derivatives thereof, suspension concentrates and derivatives thereof, and any other liquid or solid form composition that includes a herbicide compound. Other examples may include wettable powders, water dispersible granules, other types of granules, water-soluble powders, emulsifiable concentrates, oil-based flowables, concentrated emulsions, suspo-emulsions, emulsions, suspensions, mixtures, dispersions, and derivatives of any of these and others, any of which include a herbicide compound in acid form, and can further include or be combined with acidifying agent.

Different classes of herbicide compounds and different specific herbicide compounds within these classes can be used to prepare herbicide compositions according to the invention. A large variety of herbicide compounds are well known and commercially available, and one of skill will be able to identify herbicide compounds useful according to the invention, based on the present description. Suitable herbicide compounds can include herbicide compounds that act as pre-emergent or post-emergent systemic herbicides, and that can exist in an acid form. Compositions and methods of the invention are particularly beneficial when using herbicides having post-emergent activity, i.e., systemic herbicidal activity toward established plants, due to the improvements in post-emergent, systemic activity available with these compositions and methods. While wishing not to be bound by theory, it is believed that the use of a herbicide compound in acid form, especially applied directly to a plant, and especially in a herbicide composition having an acidic and a relatively low pH (e.g., below 7, 6, or 5, or below the pKa of a herbicide compound, or lower) can effect improvements in plant control by one or both of the following mechanisms. First, a charge-neutral molecule (such as an acid) can have an easier time penetrating a cuticle on a plant compared to a charged molecule (e.g., salt). Secondly, when the herbicide compound in acid form is applied with a herbicide composition containing an acidifying agent and at a low pH, the acidifying agent and low pH can have a damaging effect on a plant's surface, thereby allowing more herbicide compound to penetrate the plant surface. Separately, acid forms of herbicide compounds, due to their uncharged state, can be advantageously less affected or unaffected by hard water, e.g., less susceptible to de-activation by hard water.

Herbicide compounds may typically be available in ester or salt forms, and many herbicide compositions are conventionally sold commercially in either a salt or ester form, which are often considered to be relatively soluble, dispersible, or emulsifiable in water, as opposed to acid forms which are often less soluble in water. Acid forms of herbicides are used according to the invention.

"Herbicide compound in acid form," as used herein, refers to a herbicide compound that exists in a form of the compound that is considered to be the "acid" form of the compound, as opposed to a different chemical form of the same compound such as a salt or an ester form. Many herbicide compounds are capable of existing in discernible, understood, chemically different forms, including, e.g., an acid form, an ester form, or a salt form. The term "herbicide compound in acid form" includes herbicide compounds of these types, when the compound is in the acid as opposed to an ester or a salt form.

One way of identifying a herbicide compound in acid form is to reference a pKa of a herbicide compound. The pKa of a herbicide compound is understood to refer to the negative logarithm (base 10) of the equilibrium constant K for the reaction of the herbicide compound between its acid form and its neutral form. Methods of determining the pKa for a herbicide compound will be readily understood by the skilled artisan. Exemplary herbicide compounds that are capable of existing in an acid form can have a pKa below about 6, or below about 5 or 4. Some herbicide compounds include more than one acidic hydrogen and therefore have more than a single pKa value. According to the invention, the relevant and referred to pKa is the pKa of a herbicide compound that relates to the change of the compound between the compound considered to be the deprotonated "acid" form of the compound, and what is considered to be the protonated (neutral) form of the "acid." The deprotonated acid form of the compound predominates at pH below the pKa, and the protonated form predominates at pH above the pKa. Examples of pKa values for certain herbicide compounds are included in the Table 1.

Some examples of useful herbicide compounds that can be used in their acid forms according to the invention include the following, some or all of which are commercially available in their acid form (though presently not generally sold in that form as herbicide formulations). For herbicide compounds that are sold in forms other than the acid form, such as a salt or ester form, a skilled chemist will understand how to convert the non-acid to an acid form for use as described herein.

The class of phenoxy herbicides generally includes herbicides derived from chlorinated phenols, and includes herbicide compounds that can exist in an acid form. Examples include the well known herbicides 2,4-dichlorophenoxyacetic acid (known as 2,4-D), 4-methyl-2-chlorophenoxyacetic acid (MCPA Acid), and 2(-2-methyl-4-chlorophenoxy)propionic acid (MCPP acid), as well as others.

Pyridine herbicides are herbicides derived from a pyridine ring-containing compound, and include herbicide compounds that can exist in an acid form. Examples include 3,5,6-trichloro-2-pyridyloxyacetic acid (triclopyr acid) and fluoroxypyr (4-amino-3,5-dichloro-6-fluoro-2-pyridyloxyacetic acid), as well as others.

Benzoic acid herbicide compounds include or are derived from benzoic acid compounds. This class of herbicide compounds includes herbicide compounds that can exist in an acid form. A single example is dicamba acid (3,6-dichloro-O-anisic acid), but others could also be used according to the invention.

Aryloxy phenoxy propionic acid herbicide compounds (also referred to sometimes as "oxyphenoxy" herbicides), are another class of herbicide that can exist in an acid form. Examples of specific compounds include fluazifop acid, quizolofop acid, as well as others.

Imidazolinones are still another class of herbicide compounds that can exist in acid form, with specific examples including imazethapyr acid, imazaquin acid, imazapyr acid, imazamethbenz acid, imazapic acid, and imazamox acid. See infra.

TABLE 1

| Acidic Herbicide | pKas | Trade Name | Salt Form | Herbicide Family | Sub Family |
|---|---|---|---|---|---|
| Bromoxynil | 4.06 | BUTRIL | | Benzonitrile | |
| loxynil | 3.96 | | | Benzonitrile | |
| Bentazon | NA | BASAGRAN | sodium | Non-Family | |
| Dicamba | 1.87 | BANVEL | diglycolamine diethylamine | Growth Regulator | Bezoic Acid |
| Diclofop | 3.57 | HOELON | | Aryloxyphenoxy-propionate | |
| Fenoxaprop | NA | PUMA | | Aryloxyphenoxy-propionate | |
| Fluazifop-p | 2.98 | FUSILADE | | Aryloxyphenoxy-propionate | |
| Fosamine | NA | KRENITE | | Non-Family | |
| Glufosinate | 2, 2.9 | LIBERTY | ammonium | Phosphorylated amino acid | |
| Glyphosate | 2.6, 5.6 | ROUNDUP | Isoproplyamine | Non-Family | |
| Haloxyfop | 4.33 | VERDICT | | Aryloxyphenoxy-propionate | |
| Imazamethbenz | 2.9 | ASSERT | | Imidazolinone | |
| Imazapyr | 2, 3 | ARSENAL | Isoproplyamine | Imidazolinone | |
| Imazaquin | 3.8 | SCEPTER | ammonium | Imidazolinone | |
| Imazamox | | RAPTOR | | Imidazolinone | |
| Imazethapyr | 3.9 | PURSUIT | ammonium | Imidazolinone | |
| Picloram | 2.3 | TORDON | triisopropanolamine | Growth Regulator | Pyridine |
| Triclopyr | 2.68 | GARLON | triethylamine | Growth Regulator | Pyridine |
| Clopyralid | 2.3 | STINGER | monoethanolamine | Growth Regulator | Pyridine |
| Floroxypyr | | STARANE | | Growth Regulator | Pyridine |
| Quinclorac | 4.34 | FACET | | Growth Regulator | Quinolinic Acid |
| Quizalofop-p | NA | ASSURE | | Aryloxyphenoxy-propionate | |
| Sethoxydim | 4.16 | POAST | | Cyclohexanedione | |
| 2,4-D | 2.8 | | sodium ammonium triethanolamine dimethylamine | Growth Regulator | Phenoxy Carboxylic |
| 2,4-DB | 4.8 | | | | Phenoxy Carboxylic |
| Dichlorprop | 2.86 | | dimethylamine | Growth Regulator | Phenoxy Carboxylic |
| MCPA | | | | Growth Regulator | Phenoxy Carboxylic |
| Mecoprop (MCPP) | | | | Growth Regulator | Phenoxy Carboxylic |
| Clethodim | | SELECT | | Cyclohexanedione | |
| Sethoxydim | | | | | |
| Acifluorfen | 3.86 | BLAZER | sodium | Diphenyl Ether | |
| Dacthal | | | | Phthalic Acid | |
| Endothal | | | | Phthalic Acid | |
| Alanap | | | | Phthalic Acid | |
| Asulam | 4.82 | | | Non-Family | |

(Where a pKa is not included, the skilled artisan will be able to determine pKa.)

The herbicide compositions of the invention also include an acidifying agent. The acidifying agent can be any acidic material that can be used to reduce the pH of the herbicide composition and preferably maintain the pH at a level that will allow the herbicide compound to exist in its acid form, e.g., at a pH below 7, preferably below the pKa of the herbicide compound.

A variety of different acidifying agents can be useful in the herbicide compositions of the invention, e.g., to improve efficacy of a herbicide composition. Examples of a certain type of acidifying agent are described in U.S. Pat. Nos. 4,445,925, 4,994,101, 5,288,692, (to Young) the disclosures of which are incorporated herein by reference. Other exemplary acidifying agents are known, and still others are described herein, as well as in Assignee's U.S. patent application Ser. No. 10/103,493, filed Mar. 21, 2002, entitled HERBICIDE COMPOSITIONS COMPRISING SUSPENSION CONCENTRATE WITH GLYPHOSATE ACID, METHODS OF PREPARATION, AND METHODS OF USE, and U.S. Pat. No. 6,803,345, granted Oct. 12, 2004, entitled HERBICIDE MICROEMULSION-FORMING-CONCENTRATES, MICROEMULSIONS, AND METHODS, each of which is incorporated herein by reference.

The acidifying agent chosen and the amount included in a herbicide composition can be based on factors such as the intended application (including the identity of the undesirable plant growth, and the desired plant growth), the method of application, the herbicide compound chosen and the type of herbicide application composition, physical and chemical properties of the herbicide application composition, and other factors. The acidifying agent may be any of a variety of suitable organic and inorganic acids, of any useful strength or concentration (e.g., concentrated or diluted), that can be included in a herbicide composition, preferably without causing substantial or undue negative effects on the herbicide composition such as reaction with another ingredient of the composition such as the herbicide compound, precipitation, etc.

Non-limiting examples of specifically useful acidifying agents include acids such as sulfuric acid, phosphoric acid, hydrochloric acid, nitric acid, acetic acid (e.g., "glacial" acidic acid), perchloric acid, polyphosphoric acid, acidic adducts such as the sulfuric acid adducts described in U.S. Pat. No. 5,288,692 (Young), especially the adduct of sulfuric acid and urea, and any other composition that can be used to affect the pH of a herbicide composition. It will be understood that such acidifying agents can be used alone or in combination, and can be included in a herbicide composition in a concentrated or a diluted form.

Just one example of a useful class of acidifying agent is the class of adducts of sulfuric acid and an "amide" according to the formula:

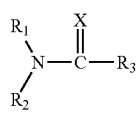

(1)

wherein X is chalcogen, and each of $R_1$, $R_2$, and $R_3$ is independently selected from hydrogen and organic radicals. As used herein, "amide" encompasses all compounds of formula (1) regardless of the chalcogen. The molar ratio of amide to acid is usually in the range of about ¼ to less than 2 so that at least some of the acid is present as the monoamide-acid adduct.

When $R_1$, $R_2$, and $R_3$ are organic radicals, they may be cyclic or acyclic, straight, or branched chained, and can contain one or more heteroatoms such as sulfur, nitrogen, oxygen, phosphorus and the like. Further, $R_1$, $R_2$, and $R_3$ can contain one or more substituents such as thiol, hydroxy, nitro, amino, nitrile, amide, ester and halogen groups and others. Such organic radicals may contain aryl groups such as aralkyl and alkaryl groups. Certain preferred organic radicals can be free of olefinic or alkynyl unsaturation and can generally have up to about 20, preferably up to about 10 carbon atoms. Particularly preferred amides include urea, thiourea, formamide, dimethylformamide, biuret, triuret, thioformamide, and combinations of these.

The chalcogens are elements of Periodic Group VI-B and include oxygen, sulfur, selenium, tellurium, and polonium. Oxygen and sulfur can be preferred due to low cost, availability, low toxicity, and chemical activity, and oxygen is the most preferred.

An example of a specific compound of formula (1) is the sulfuric acid/urea adduct:

(2)

Other types of useful acidifying agents, as stated, include sulfuric acid, phosphoric acid, hydrochloric acid, nitric acid, acetic acid (e.g., "glacial" acidic acid), perchloric acid, polyphosphoric acid, other adducts, etc. Various such acids are commercially available in different forms and concentrations, including solids, liquid solutions, concentrated or diluted liquid solutions, etc., or can be prepared by one of skill. Any such form of acidifying agent may be useful to reduce the pH of a herbicide composition, preferably without causing undue negative effects on the herbicide composition. The chosen form of an acidifying agent may be based on factors such as commercial availability, convenience, and the overall desired properties of the herbicide composition, its different ingredients (e.g., the herbicide compound), and desired methods of preparation and use.

The particular amount of acidifying agent included in a herbicide composition can be selected depending on factors such as the particular composition and chemistry of the herbicide application composition, including the amounts and chemistries of other ingredients of the compositions such as surfactants and the herbicide compound; the amount and identity of any solvent; whether water is included and in what amount; the type of acidifying agent and its chemistry, form (e.g., liquid, solid, concentrated, or diluted) and strength (concentration); and the desired pH of the herbicide composition and the relevant pKa of the herbicide compound. Preferred amounts of any particular acidifying agent can be capable of improving the efficacy of a herbicide composition, and will be sufficient to produce an application composition having a pH below the pKa of the herbicide compound, as discussed.

The herbicide composition may be prepared from various different herbicide compositions and herbicide composition precursors or concentrates. Generally, the herbicide compositions of the invention can be prepared from any type of precursor herbicide compositions. Non-limiting examples of herbicide composition precursors include microemulsion-forming concentrates or microemulsions and derivatives thereof, and suspension concentrates and derivatives thereof. Other examples may include wettable powders, water dispersible granules, other types of granules, water-soluble powders, emulsifiable concentrates, oil-based flowables, concentrated emulsions, suspo-emulsions, emulsions, suspensions, mixtures, dispersions, the derivatives of any of these and others. Any of these or other types of herbicide compositions, precursors, or concentrates, can be used in manners known in herbicide and chemical arts, in combination with an acidifying agent according to the invention. A couple of preferred methods of preparing herbicide compositions according to the invention include preparation from microemulsion-forming-concentrates, microemulsions, and suspension concentrates, combined with acidifying agent. As will be readily apparent to those skilled in the herbicide arts, however, and as stated above and elsewhere in the present description, other types of herbicide compositions, herbicide composition precursors, and concentrates, will be useful when combined with acidifying agent according to the invention and present description.

One method of preparing herbicide compositions of the invention is from microemulsions or microemulsion-forming-concentrates. See, Applicants' U.S. Pat. No. 6,803,345 entitled "Herbicide Microemulsion-Forming-Concentrates, Microemulsions, and Methods."

The term "microemulsion" means a solution that contains an oil phase and water, wherein the oil phase is finely dispersed such that light passes through the microemulsion solution and the microemulsion may be opaque or clear in appearance. Microemulsions are known types of compositions, and are sometimes considered either as micellar solutions containing inverted micelles (hydrophobic tails oriented toward the external oil phase and hydrophilic heads in the inner core) with water solubilized in the inner core, or as emulsions containing tiny droplets of water surrounded by an interfacial film. See, e.g., *Surfactants and Interfacial Phenomena*, Milton J. Rosen, Page 239&240, John Wiley & Sons (1978). Microemulsion-forming-concentrates or "MFCs" include a herbicide compound (in acid form) dissolved in surfactant, optionally water, optionally may but preferably do not include added organic solvent, and can be diluted with water to form a microemulsion. MFCs can typically be translucent, opaque, or even clear solutions.

The herbicide compound in acid form can be dissolved in surfactant (and optionally water and organic acid) to form an MFC that contains surfactant and dissolved herbicide compound in acid form.

A very large variety of surfactants are known and commercially available, including such different classes as cationic surfactants, anionic surfactants, non-ionic surfactants, ionic surfactants, and amphoteric surfactants. The surfactant can be any surfactant or combination of two or more surfactants useful to dissolve the herbicide compound in its acid form. Examples of some preferred surfactants include cationic, non-ionic, and anionic surfactants. Of these, some even more specific types of preferred surfactants include non-ionic linear or branched alcohol ethoxylate surfactants, anionic phosphoric acid ester surfactants (sometimes referred to as "phosphate ester" surfactants), and cationic ethoxylated tallow amine surfactants. Examples of surfactants and identification of their intermediate and general classifications are as follows:

An anionic surfactant is a surface-active molecule in which an active portion of a lipophilic portion of the molecule forms a negative ion (i.e., anion) when placed in aqueous solution. Exemplary anionic surfactants include phosphoric acid ester surfactants (sometimes referred to as "phosphate ester" surfactants), sodium alkyl naphthalene sulfonate surfactants, and ethoxylated tristyrylphenol phosphate salts.

Exemplary sodium alkyl naphthalene sulfonate surfactants include sodium butyl naphthalene sulfonate, sodium di-n-butyl naphthalene sulfonate, sodium diisopropyl naphthalene sulfonate, sodium dimethyl naphthalene sulfonate, and mixtures thereof. Sodium butyl naphthalene sulfonate is commercially available, for example, under the trade name "MOR-WET B" from Witco/Crompton, Greenwich, Conn. Sodium di-n-butyl naphthalene sulfonate is commercially available, for example, under the trade name "MORWET DB" from Witco/Crompton, Greenwich, Conn. Sodium diisopropyl naphthalene sulfonate is commercially available, for example, under the trade name "MORWET IP" from Witco/Crompton, Greenwich, Conn. Sodium dimethyl naphthalene sulfonate surfactant is commercially available, for example, under the trade name "SELLOGEN HR" from Henkle Corp., Cincinnati, Ohio.

An exemplary ethoxylated tristyrylphenol phosphate potassium salt surfactant is commercially available, for example, under the trade name "SOPROPHOR FLK" from Rhodia, Cranbury, N.J.

A nonionic surfactant is a surface-active molecule that does not contain ionizable polar end groups but does contain hydrophilic and lipophilic portions. Exemplary nonionic surfactants include polyoxyethylene alkylether or alkenylether surfactants. Nonionic surfactant used to prepare a suspension concentrate as described herein may include long or short chain alcohol ethoxylate surfactant. The alcohol ethoxylate surfactant may be branched or linear.

An example of a useful nonionic polyoxyalkylene surfactant includes alcohol ethoxylate having the general formula:

$$R\text{—}O\text{—}((CH_2)_xO)_y\text{—}H$$

wherein R may be "long" or "short" chain and "branched" or "linear" alkyl. R preferably can be a "short chain" branched or linear alcohol, meaning that it can have from about 3 to 23 or fewer carbon atoms. With respect to the oxyalkylene, x can preferably be in the range from about 2 to 5, preferably from

SURFACTANTS

| TRADE NAME | COMMON NAME | INTERMEDIATE CLASSIFICATION | GENERAL CLASSIFICATION |
|---|---|---|---|
| Tomadol 1-5 | 11 carbon 5 mole linear alcohol | ethoxylated linear alcohol | nonionic |
| Tomadol 1-7 | 11 carbon 7 mole linear alcohol | ethoxylated linear alcohol | nonionic |
| Surfonic L12-6 | 12 carbon 6 mole linear alcohol | ethoxylated linear alcohol | nonionic |
| Trymeen 6607 | 20 mole tallow amine | ethoxylated amines/amide | cationic |
| Stepfac 8170 | phosphate ester | phosphate ester | anionic |
| Surfonic PE 1218 | phosphate ester | phosphate ester | anionic |
| Surfonic DDA6 | 6 mole branched alcohol ethoxylate | branched alcohol ethoxylate | nonionic |
| Surfonic TDA6 | 6 mole tridecyl alcohol | branched alcohol ethoxylate | nonionic |
| Surfonic T-15 | 20 mole tallow amine | ethoxylated amines/amide | cationic |
| Surfonic OP-70 | 7 mole octylphenol | ethoxylated alkyl phenol | nonionic |
| Tergitol NP-6 | 6 mole nonylphenol | ethoxylated alkyl phenol | nonionic |
| Trylox 5902 | 16 mole castor oil | ethoxylated fatty acids/oils | nonionic |
| Span 80 | sorbitan laurate | sorbitan laurate | nonionic |
| Tween 80 | polysorbate 80 | sorbitan oleate | nonionic |
| Soprophor 796P | tristerol phenol EO/PO | propylated, ethoxylated fatty acid, alcohols, or alkyl phenols | nonionic |
| Surfonic L24-5 | 24 carbon 5 mole linear alcohol | ethoxylated linear alcohol | nonionic | about 2 to 4 (e.g., 2 or 3, for a polyoxyethylene or polyoxypropylene, respectively) and y can preferably be in the in the range from 5 to 25.

Examples of useful short chain nonionic polyoxyalkylenes include linear alcohol polyoxyethylenes having the general formula:

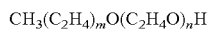

wherein $CH_3(C_2H_4)_m$ is a short chain linear alkyl having from about 3 to 23 or fewer carbon atoms (i.e., m can be in the range from about 1 to 11 carbon atoms), and n is in the range from about 5 to 25.

Another example is short chain nonionic polyoxypropylenes having the general formula:

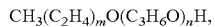

wherein $CH_3(C_2H_4)_m$ is a short chain linear alkyl having from about 3 to 23 or fewer carbon atoms (i.e., m can be in the range from about 1 to 11 carbon atoms), and n can preferably be in the range from about 5 to 25.

Exemplary short chain linear alcohol ethoxylate surfactant are commercially available, for example, under the trade names "SURFONIC L12-6" from Huntsman, Austin, Tex., "SURFONIC L24-7" from Huntsman, Austin, Tex., "TERGITOL 15-S-7", "TERGITOL 24-L-60", "ALPHONIC 1012-60", "ALPOHONIC 1414-60", "BIOSOFT ET 630," from Stepan Company, Chicago, Ill., and "GENOPAL 24-L-60."

Other exemplary surfactants include polyethylene glycol, fatty acid 30 ethoxylates, phosphate esters, octyl phenol ethoxylates, and nonyl phenol ethoxylates.

Useful polyethylene glycol surfactants are commercially available, for example, under the trade names "ADEKA PEG" from Asahi Denka Kogyo, Tokyo, Japan.

Useful fatty acid ethoxylate surfactants are commercially available, for 5 example, under the trade names "NINEX MT-610", "NINEX MT-615", and "NINEX MT-630" from Stepan, Northfield, Ill.

Useful phosphate ester surfactants are commercially available, for example, under the trade names "STEPFAC 8180", "STEPFAC 8181", and "STEPFAC 8182" from Stepan.

Useful octyl phenol ethoxylate surfactants are commercially available, for example, under the trade name "MAKON OP-9" from Stepan, Northfield, Ill.

Useful nonyl phenol ethoxylate surfactants are commercially available, for example, under the trade names "MAKON 4", "MAKON 6", "MAKON 8", "MAKON 10", "MAKON 12", and "MAKON 14" from Stepan, Northfield, Ill.

A cationic surfactant is a surface-active molecule in which an active portion of a lipophilic portion of the molecule forms a positive ion (i.e., cation) when placed in aqueous solution. In one embodiment, exemplary cationic surfactant includes ethoxylated tallow amine.

Generally speaking, the amounts of surfactant and herbicide compound in an MFC can be any useful amounts, meaning that the amounts are sufficient to produce a useful herbicide composition or a useful herbicide composition precursor, based on the amount of herbicide compound dissolved in surfactant. Amounts of either organic solvent or water may also be used to produce an MFC, but it is preferred that only small amounts of organic solvent and more preferably no organic solvent be added to the MFC. Useful relative amounts of herbicide and surfactant will vary for different herbicide compounds and different surfactants, as well as the optional presence of organic solvent or water. Exemplary MFCs can include from about 10 to about 40 parts by weight, e.g., from about 20 to about 35 parts by weight herbicide compound in acid form, and from about 60 to about 90, e.g., from about 65 to about 80 parts by weight surfactant. Useful amounts of herbicide compound in acid form and surfactant can of course be outside of these recited ranges, depending on preference, and on factors such as the solubility of the herbicide compound and whether an organic solvent or water is also present.

MFCs can be prepared by any methods useful to dissolve a herbicide compound in acid form in a surfactant. In general, the herbicide compound in acid form can typically be provided as a solid, but other, non-solid forms may also be available and useful, such as liquid oil soluble acid herbicide compounds. An amount of the herbicide compound in acid form can be dissolved into a surfactant by selecting a proper surfactant or combination of surfactants (combinations of two or more surfactants will be referred to collectively herein as "surfactant"), each in useful amounts. Heat can optionally be used to facilitate dissolution of herbicide compound in surfactant. For example a mixture of herbicide compound and surfactant (with optional organic solvent) may be heated at a temperature, e.g., in the range from about 100 F to about 200 F, preferably from about 130 F to about 150 F, to facilitate dissolution of the herbicide compound in the surfactant. Organic solvent or water may also be added to the mixture to facilitate dissolution, although it can be preferred to avoid the use of organic solvents. Agitation or other techniques may be used to encourage dissolution.

Other ingredients such as antifoaming agents may be included in the MFC or microemulsion, as necessary, and in amounts and using techniques that will be well understood. If an acidifying agent is added directly to a MFC or microemulsion, the acidifying agent can be added at any stage, e.g., by simple combining and mixing of acidifying agent and MFC or microemulsion.

The MFC can be diluted with water to produce a microemulsion. Relative amounts of MFC and water used to prepare a microemulsion can be any amounts that produce a useful microemulsion, and can depend on factors such as the composition of the MFC (e.g., the type and concentration of the herbicide compound), the intended application (including the plant to be controlled or the crop to be protected), the mode of application (e.g., field or aerial spraying or application from a hand-held spray applicator, or other technique), etc.

Although amounts outside of the following ranges can also be useful, and exact ratios can depend significantly on the identity of herbicide compound used, exemplary MFCs can be combined with water to form a microemulsion by mixing about 0.05 to about 7 parts by volume MFC with from about 93 to about 99.95 parts by volume water (e.g., 2 ml MFC to 98 ml water, 1 quart MFC to 12 gallons water, 12 oz. MFC to 20 gallons water, 0.065 parts MFC to 99.935 parts water, or equivalent amounts or different of each). The actual amount of MFC to water can vary depending on the herbicide compound, the crop or weed species, the amount of spray volume as chosen by the applicator, the desired strength of the application composition, whether other ingredients are added, etc. This composition may be applied as a herbicide application composition, optionally additionally including other ingredients such as a desired amount of acidifying agent or one or more other herbicide compound or composition.

Another method of preparing a herbicide composition of the invention is from a suspension concentrate, especially a suspension concentrate compositions that includes glyphosate acid, i.e., glyphosate (N-(phosphonomethyl)glycine) in the acid form, or a suspension concentrate that contains an imidazolinone compound in acid form.

The glyphosate active herbicide compound (N-(phosphonomethyl)glycine) includes 4 acidic protons which are removed at $pKa_1$ of 0.8 ($1^{st}$ phosphonic), $pKa_2$ 2.3 or 2.6 (carboxylate), $pKa_3$ 6.0 ($2^{nd}$ phosphonic), and $pKa_4$ 11.0 (amine). For purposes of the present description, when discussing the pKa of the glyphosate acid form of the N-(phosphonomethyl)glycine, the $pKa_2$ is specifically meant, because this is the pKa that relates to the conversion of the glyphosate compound to and from the carboxylic acid form, which is generally considered to be the "acid" form of the glyphosate herbicide compound. See, for example, http://www.soils.wisc.edu/virtual_museum/glyphosate/glyphosate_tx.html, which is part of the Virtual Museum of Minerals and Molecules, originally released 25 Dec., 1999, and last modified 31, Dec., 2000.

Glyphosate acid is commercially available, generally in the form of a granular, solid, powder form or as a wet cake, for example from Dow Chemical Co., under the trade name Glyphosate WC. These materials are sold in the form of solid glyphosate acid particles having an average size (diameter) in the range from about 5 to about 18 microns.

Glyphosate acid can be incorporated into a suspension concentrate, e.g., as described in Assignees' copending United States Patent Application entitled "Herbicide Compositions Comprising Suspension Concentrate with Glyphosate Acid, Methods of Preparation, and Methods of Use," filed on Mar. 21, 2002, and having U.S. Ser. No. 10/103,493. The term "suspension concentrate" as used herein, means a composition also sometimes referred to as an "aqueous flowable" or a "water-based flowable" composition, which compositions are known in the herbicide art and include or consist of particles of a generally insoluble solid active herbicide compound in suspension (preferably concentrated suspension) in water. The suspension concentrate can be produced with particles of glyphosate acid by suspending and preferably dispersing the particles in water with the assistance of other ingredients such as conventional dispersants, surfactants (wetting agents), and other optional ingredients. The glyphosate acid should be in the form of particles that exhibit physical characteristics such as size, shape, etc., that will allow the glyphosate acid particles to be suspended in water as described. The particle size range can vary depending on factors such as the other ingredients used to prepare the suspension concentrate and their respective amounts, but exemplary particles may be in the size range below about 10 microns, for example in the range from about 4 or 5 to about 7 or 8 microns.

The suspension concentrate includes water in a useful amount, such as an amount that, in combination with one or more other ingredients described herein (e.g., such as surfactant and/or dispersant) will allow suspension and preferably dispersion of the glyphosate acid particles. Exemplary amounts of water in a suspension concentrate may be, for example, in the range from about 20 to about 60 weight percent water based on the total weight of the suspension concentrate, such as from about 30 to about 50 weight percent water in a suspension concentrate.

A wetting agent, (also referred to herein as "surfactant"), can be used to facilitate suspending the glyphosate acid particles in a suspension concentrate. A very large variety of surfactants are known and commercially available, including such different classes as cationic surfactants, anionic surfactants, non-ionic surfactants, ionic surfactants, and amphoteric surfactants, etc. According to the invention, the surfactant can be any surfactant or combination of surfactants useful to suspend particles of glyphosate acid. Examples of some preferred surfactants include cationic, non-ionic, and anionic surfactants, either alone or in combinations (e.g., blends of cationic and nonionic surfactants). Of these, particular types of preferred surfactants include non-ionic linear or branched alcohol ethoxylate surfactants, anionic phosphoric acid ester surfactants (sometimes referred to as "phosphate ester" surfactants), and cationic ethoxylated tallow amine surfactants. An example of a useful type of surfactant includes nonionic wetting agents, such as Surfonic L12-6, from Huntsman.

Examples of commercially available surfactants useful as wetting agents or dispersants include those identified in the list of surfactants above relating to microemulsion-forming-concentrates and the following:

| TRADE NAME | COMMON NAME | FUNCTION | GENERAL CLASSIFICATION |
|---|---|---|---|
| Tomadol 1-5 | 11 carbon 5 mole linear alcohol | wetting agent | nonionic |
| Surfonic L12-6 | 12 carbon 6 mole linear alcohol | wetting agent | nonionic |
| Trymeen 6607 | 20 mole tallow amine | wetting agent/adjuvant | cationic |
| Stepfac 8170 | phosphate ester | dispersant/adjuvant | anionic |
| Surfonic PE 1218 | phosphate ester | dispersant/adjuvant | anionic |
| Surfonic OP-70 | 7 mole octylphenol | wetting agent/adjuvant | nonionic |
| Tergitol NP-9 | 9 mole nonylphenol | wetting agent/adjuvant | nonionic |
| Soprophor 796P | tristerol phenol EO/PO | dispersant | nonionic |
| Soprophor FLK | tristerolphenol potassium phosphate | dispersant | anionic |
| Polyfon H | sodium lignosulfonate | dispersant | anionic |
| Morwet D425 | napthalene formaldehyde condensant | dispersant | anionic |
| Morwet IP | naphthalene sulfonates | wetting agent | anionic |
| Pluronic L1061 | block copolymer | dispersant | nonionic |
| Tersperse 4984 | block copolymer/alcohol ethoxylate | dispersant, wetting | nonionic |
| Tersperse 2500 | surfactant | dispersant | anionic |
| Surfonic DOS60 | sulfosuccinate | wetting agent | anionic |
| LI-700 | lecithin derivative | adjuvant | nonionic |
| Goodrite K732 | polyacrylic acid | dispersant | anionic |

The amount of surfactant ("surfactant" refers to one or a combination of surfactants) can be any amount that will allow the preparation of a suspension concentrate. Useful amounts of surfactant or wetting agent will be apparent to the skilled artisan based on this overall description, with exemplary amounts being below about 20 percent by weight surfactant or wetting agent based on the total weight of the suspension concentrate, and with preferred amounts possibly being in the range from about 0.1 or 1 to about 10 or 15 weight percent surfactant based on the total weight of the suspension concentrate, with the range from about 0.5 to 3 weight percent being particularly preferred.

A dispersant can also be useful to facilitate preparation of a suspension concentrate containing glyphosate acid particles. An example of a useful type of dispersant would include nonionic dispersants, such as Tersperse 4892, from Huntsman. The amount of dispersant can be any amount that will allow the preparation of a suspension concentrate, and that may help to stabilize a suspension concentrate, e.g., by preventing flocculation. Exemplary amounts of dispersant can be below about 10 or 8 percent by weight dispersant based on the total weight of the suspension concentrate, with preferred amounts being from about 2 to about 6 weight percent dispersant, based on the total weight of the suspension concentrate.

Other ingredients or additives can also be included in the suspension concentrate. For example, an antifreeze may be useful, such as propylene glycol or other low molecular weight alcohols or polyols, in an amount to reduce the freezing point of the suspension concentrate, e.g., below about 20 weight percent based on the total weight of the suspension concentrate, for example from 1 to about 15 weight percent, or from about 5 to about 10 weight percent.

Thickeners can be included in the suspension concentrate in amounts useful to provide gravitational stabilization by increasing viscosity. Useful thickeners include chemical compounds and polymeric materials that will be known to and understood by the skilled artisan, and include, generally, natural and synthetic starches, gums, and other types of chemical compounds that will increase the viscosity of a solution. Thickening agents are well known in the chemical and polymer arts, and include, inter alia, polyacrylamides, cellulosic resins and functionalized cellulosic resins, polyacrylic acids, polyethylene oxides, and the like. Commercially available examples include Kelzan and Rhodaopl xanthan gums, Attagel 50 and Attaflow FL clays, Carbopol 910 polyacrylic acid polymer, Kelcosol sodium alginate, and Bentalite purified Bentonite. Amounts of thickener below about 15 or 10 weight percent based on the total weight of the suspension concentrate, may generally be useful. Preferred amounts may be less than 0.5 weight percent for gums or cellulose resins.

Another ingredient in a suspension concentrate can include an antifoaming agent, with typical amounts being less than 1 percent by weight, e.g., less than 0.5 percent by weight.

Other useful additives to the suspension concentrate may include other surfactants, antimicrobial agents, anticorrosion agents, and other ingredients that will be understood to be useful, in amounts that will also be understood. Surfactants having functions of wetting, spreading, or penetrating, preferably to improve the efficacy of a herbicide composition, may also be added to a herbicide composition, e.g., as a tank mix ingredient. Organic solvents may be included in the suspension concentrate if desired, but are generally not used or needed.

Ingredients of a suspension concentrate can be combined by know methods, including mixing, agitating, and dispersing, and, if needed or otherwise desired, milling of the glyphosate acid particles, to produce the suspension concentrate. Any of the mixing, milling, agitating, dispersing, or combining steps can be done in any order, such as milling the glyphosate acid particles and adding the milled particles to water and other ingredients, or by adding the particles to water and other ingredients followed by wet milling.

One exemplary method of producing a suspension concentrate starts with glyphosate acid particles in the form of a wet cake or dry (granular, powder) acid, generally having a relatively large particle size (e.g., greater than about 10 microns). The wet cake or dry particles of that size can be mixed or dispersed into a liquid. This can be done, for example, by combining the glyphosate acid particles with water and other ingredients with agitation or mixing to disperse the particles into the water. For example, the glyphosate acid particles can be added to water and one or more of surfactant, dispersant, antifreeze, and antifoam, and mixed using a high-speed mixer to disperse the glyphosate acid particles. The mixture of glyphosate acid, water, and other ingredients can be further processed toward a suspension concentrate by methods that will process the glyphosate acid particles into a form that allows suspension of the particles in water in the form of a suspension concentrate, for instance by reducing the size of the particles in the presence of a useful surfactant. Thus, a processing step can be to reduce the size of glyphosate acid particles to a size that will allow the particles, in combination with one or more of the other ingredients described herein such as surfactant and/or dispersant, to be maintained in a stable suspension concentrate composition. An exemplary method of reducing the size of the glyphosate acid particles is by using milling techniques, e.g., what is referred to as "wet milling." Any method of reducing particle size may be useful, such as by using an attrition mill, ball mill, sand mill, or other wet milling process.

After reduction of the particle size, the solution containing the suspended glyphosate acid particles can be further combined with a thickener, by mixing the thickener into the solution.

The herbicide compound in acid form can also be an imidazolinone acid, for example, as described in Applicants' U.S. Pat. No. 6,703,346 entitled "Herbicide Compositions Comprising Imidazolinone Acid, Methods of Preparation, and Methods of Use." Imidazolinone compounds, and chemical derivatives thereof, are a known type of active herbicide compound. Imidazolinone is generally available in either the acid or salt form. The salt forms are considered to be generally soluble in water, whereas the acid forms are considered to be generally insoluble in water.

Imidazolinone in the acid form is considered to be generally an insoluble active herbicide compound. This means, for example, depending on temperature and pH, that imidazolinone acid can be soluble in water or acidic water only up to a few weight percent, meaning that approximately 100 grams of an aqueous solution can dissolve only approximately a couple of grams of imidazolinone acid, e.g., approximately 1 gram, or one weight percent.

Examples of imidazolinone acids include imazethapyr acid, imazaquin acid, imazapyr acid, imazamethabenz acid, imazapic acid, imazamox acid, and combinations thereof. Imazethapyr acid has the molecular formula $C_{15}H_{19}N_3O_4$ and is commercially available generally in the form of a powdered solid, under the trade designation "PURSUIT." Imazaquin acid has the molecular formula $C_{17}H_{17}N_3O_3$ and is commercially available generally in the form of a powdered solid, under the trade designation "SCEPTER" and "IMAGE." Imazapyr acid has the molecular formula $C_{13}H_{15}N_3O_3$ and is commercially available generally in the form of a powdered solid, under the trade designation "ARSENAL," "CHOPPER," and "STALKER." Imazamethabenz acid has the molecular formula $C_{15}H_{18}N_2O_3$ and is commercially available generally in the form of a powdered solid, under the trade designation "ASSERT." Imazapic acid has the molecular formula $C_{14}H_{17}N_3O_3$ and is commercially available generally in the form of a powdered solid, under the trade designation "CADRE" and "PLATEAU." Imazamox acid has the molecular formula $C_{15}N_{19}N_3O_4$ and is commercially available generally in the form of a powdered solid, under the trade designation "RAPTOR" and "ODESSEY."

Exemplary imidazolinone acids described herein can generally have a pKa below about 7, especially below about 5 or 4, for example, the pKa of imazamethbenz is approximately 2.9, the pKa of imazapyr is approximately 2 or 3, the pKa of imazaquin is approximately 3.8, and the pKa of imazethapyr is approximately 3.9. Methods of determining pKa for a herbicide compound will be readily understood by the skilled artisan.

The use of imidazolinone acids can be advantageous because the acid form does not need to be converted to the imidazolinone salt form during processing or prior to application, as is often done with imidazolinone herbicide compounds, because the salt forms are more soluble in water. Instead, herbicide compositions that contain imidazolinone acid in the imidazolinone acid form, such as preferred suspension concentrates, can be simple and economical to produce, and can be efficiently distributed, prepared, and applied without taking steps to convert the imidazolinone herbicide out of its acid form. In addition, the acid form of imidazolinone compounds, due to its uncharged state, can be advantageously less affected or unaffected by hard water, e.g., less susceptible to de-activation by hard water.

In one preferred embodiment of the invention, a herbicide composition includes a suspension concentrate comprising imidazolinone acid. The suspension concentrates can be produced with particles of imidazolinone acid compounds by suspending and preferably dispersing the particles in water with the assistance of other ingredients such as surfactant (also referred to as "wetting agents"), dispersant, and other optional ingredients.

The imidazolinone acid should be in the form of particles that exhibit physical characteristics such as size, shape, surface features, etc., that will allow the imidazolinone acid particles to be suspended in the form of a suspension concentrate, preferably an aqueous suspension concentrate. The particle size range can vary depending on factors such as the other ingredients used to prepare the suspension concentrate and their respective amounts, but exemplary particles may be in the size range below about 10 microns, for example in the range from about 4 to about 8 micrometers in diameter or from about 5 to about 7 micrometers in diameter.

Such herbicide compositions of the invention can include imidazolinone acid in a useful amount. Useful amounts of imidazolinone acid in any particular composition can depend on factors such as the exact imidazolinone compound, the intended application (including the plant to be controlled or the crop to be protected), the mode of application (e.g., field or aerial spraying or application from a hand-held spray applicator, or other technique), the method of any preparation of a herbicide application composition, the amounts and identities of other ingredients added to the herbicide composition, etc. For example, an amount that, in combination with one or more other ingredients described herein (e.g., such as surfactant and/or dispersant) will allow suspension and preferably dispersion of the imidazolinone acid particles to provide a suspension concentrate. In one embodiment, useful amounts of imidazolinone acid compound in a suspension concentrate may be, for example, in the range from about 20 to about 60 weight percent imidazolinone acid based on the total weight of the suspension concentrate. In another embodiment, useful amounts of imidazolinone acid compound in a suspension concentrate may be, for example, in the range from about 25 to about 45 weight percent imidazolinone and based on the total weight of the suspension concentrate. Exemplary concentrations of suspension concentrates prepared according to the invention can include 3 pounds of imidazolinone acid per gallon, and 4 pounds of imidazolinone acid per gallon. Other concentrations of imidazolinone acid will also be useful.

Other ingredients may be used to prepare useful suspension concentrates containing imidazolinone acids, as described above with respect to glyphosate acid suspension concentrates. Exemplary other ingredients include surfactant, dispersant, thickener, and antifoaming agent. Similarly, methods as described as useful in preparing glyphosate acid suspension concentrates can be useful in preparing suspension concentrates that contain imidazolinone acid herbicide compounds. Such ingredients and methods of preparing preferred suspension concentrates comprising imidazolinone acids, are described in Applicants' U.S. Pat. No. 6,703,346, entitled "Herbicide Compositions Comprising Imidazolinone Acid, Methods of Preparation, and Methods of Use."

Any form of the above described microemulsion-forming-concentrates, microemulsions, or suspension concentrates, or any other type of herbicide composition, can be combined with an acidifying agent and applied to plants for controlling plant growth with the herbicide being present in the composition in the form of an acid compound, when applied. The acidifying agent may be incorporated into the herbicide composition at any convenient or useful time during preparation of a herbicide composition, e.g., acidifying agent may be added to a concentrated or diluted form of a microemulsion-forming concentrate, microemulsion, suspension concentrate, or other form of herbicide composition containing a herbicide in acid form or containing a herbicide compound that will exist in the form of the acid compound once the compound is in the presence of acidifying agent.

Generally, as opposed to a precursor or a herbicide composition that exists during processing, storage, or sale, a herbicide composition as used (i.e., applied to a plant) can be referred to as a "herbicide application composition." The term "herbicide application composition" refers to a herbicide composition having a concentration of herbicide compound that would normally be applied to a field or plant to control undesired plant growth, as opposed, for example, to a composition having a higher concentration of herbicide compound that may sometimes occur in preparation, storage, shipping, or sale of a herbicide composition. It is noted that any of the herbicide compositions described herein, such as the MFC, microemulsion, or suspension concentrate, if inclusive of an acidifying agent, may be capable of controlling plant growth, e.g., if applied directly to a plant. Yet it is typical for reasons of efficiency, cost, convenience, techniques presently used in applying herbicide compositions, and environmental considerations, to use a relatively diluted form of herbicide composition to conveniently apply a specific and known amount of herbicide compound per acre or per other unit of application. By way of example, herbicide application compositions include any herbicide composition having such a specific concentration of herbicide compound for application, e.g., to a field, and may include microemulsions prepared directly by diluting an MFC with water, microemulsions or other solutions prepared by diluting an MFC with water and adding one or more other optional ingredient, and suspension concentrates or diluted suspension concentrates, etc.

The amount and strength of acidifying agent can be taken into account in deciding the order of addition of ingredients and mode of preparation of a herbicide composition. For instance, the acidifying agent may be added to a precursor of the herbicide application composition, such as an MFC, a microemulsion, a suspension concentrate, a derivative of the suspension concentrate, etc., or another type of herbicide formulation, at a time and in the manner that preferably does not have any undue negative effect on either composition. An example of a method of making a herbicide application composition would include tank mixing, meaning, for example, combining an MFC, microemulsion, or a suspension concentrate, with acidifying agent and optionally with water in a spray tank, preferably to produce a herbicide application composition having a useful concentration of herbicide compound in acid form, and also preferably having a pH below the pKa of the herbicide compound.

According to the invention, any amount of the acidifying agent can be included in the herbicide composition which will, for example, improve the efficacy of the herbicide composition, and which can preferably reduce the pH of the herbicide composition, most preferably to a pH that is below the pKa of the herbicide compound. Examples of useful amounts of acidifying agents will be quite varied, considering a variety of factors mentioned in the present description. Relatively strong concentrations of liquid (aqueous) acidifying agent solutions such as 93% liquid sulfuric acid, 72% phosphoric acid, 85% polyphosphoric acid, 90% nitric acid, 99% glacial acetic acid, etc., can be added directly or can be first diluted and then added to a herbicide composition in an amount to bring the pH to below about 7, e.g., below about 5 or 6, preferably to below the pKa of the herbicide compound. In terms of volume percent, preferred amounts are highly dependent on the identity of the acidifying agent and the herbicide composition and its pKa. Very generally speaking, useful amounts of acidifying agent in a herbicide application composition can be below about 5 or 10 volume percent, e.g., in the range from about 0.01 to about 4 volume percent, or parts by volume acidifying agent per 100 parts by volume of herbicide application composition. Of course amounts of acidifying agent outside of these ranges can also be useful, and an amount used will depend in great part on the type and strength (e.g., concentration) of the particular acidifying agent chosen, as well as the desired pH of the herbicide composition.

Herbicide compositions of the invention can be used for immediate and long-term, pre- and post-emergent control of a large variety of different forms of vegetation, particularly upon appropriate selection of the herbicide compound. As an example, a herbicide composition in a concentrated form, e.g., a microemulsion-forming-concentrate, microemulsion, or a suspension concentrate, with a desired amount of acidifying agent, may be applied directly to a plant for controlling plant growth. More typically, a herbicide concentrate such as a suspension concentrate or a microemulsion-forming-concentrate, or even a microemulsion, could be sold as a herbicide concentrate product. Such a concentrate that includes an acidifying agent, could be diluted with water, such as by tank mixing, and then applied. Alternatively, a herbicide concentrate composition could be sold and purchased in a form that does not include an acidifying agent. This composition could be combined with an acidifying agent (e.g., by tank mixing), optionally diluted, and then applied. A herbicide concentrate composition that does not contain acidifying agent could be purchased by distributors or suppliers, or directly by consumers, either one of which could add acidifying agent and optionally water, or another type of herbicide or herbicide compound.

In one embodiment of a distribution system, a herbicide concentrate composition could be sold to farming product or nursery dealers, or the like, who could dilute the concentrate composition with water and/or add an acidifying agent. This could be particularly convenient if such a dealer normally kept on hand a stock of acidifying agent such as phosphoric acid or sulfuric acid, etc. The concentrate composition, combined with an acidifying agent by the dealer, could be sold to an end consumer, who could use the herbicide composition as purchased or who could optionally further dilute the purchased herbicide composition or add other ingredients to the purchased herbicide composition such as an additional herbicide by tank mixing.

The herbicide compositions of the invention can be applied for immediate vegetation control by contact killing, by application of a herbicide composition to plants. Herbicide application compositions can contain a useful amount of herbicide compound, based on factors of efficacy and safety, etc. Similarly, the amount of herbicide application composition applied to a plant or a field will be readily understood by those of skill, based, e.g., on desired efficacy, dosage, safety, and environmental factors.

The particular amount of herbicide compound in any specific herbicide application composition will depend on factors as known and described above, and in particular on the identity of the specific herbicide compound. Advantageously, it has been found that certain preferred herbicide application compositions of the invention, in particular those that have a pH below the pKa of the herbicide compound, can be applied at lower dosages (lower amounts of herbicide compound per plant or per acre) relative to other herbicide compositions containing the same herbicide compound, but not in the acid form or not at a pH below the pKa of the herbicide compound.

Examples of dosages of herbicide compound according to the invention, especially herbicide compositions of the described pH, can be in the range from about $1/100$ or $1/10$ to about 10 pounds herbicide compound per acre, with dosages in the range from about $1/100$ or $1/10$ to about 6 pounds herbicide compound per acre being sometimes preferred, e.g., from about 0.03 to 0.5 or 1 pound per acre. More resistant plants may require higher concentrations and/or higher dosage rates. The preparation of herbicide application compositions suitable to apply useful dosages based on the concentration of herbicide compound in a microemulsion, MFC, suspension concentrate, etc., will be well understood by those of ordinary skill.

The herbicide compositions can be applied using conventional aerial and field spray techniques in field applications. The herbicide compositions can also be applied by any other useful technique, such as by spot-application to undesired plant growth using a hand-held applicator, or the like.

Advantageously, certain herbicide compositions of the invention have been found to exhibit the additional advantage of being relatively non-volatile. The advantage of non-volatile herbicide compositions are self-evident to those of skill in the herbicide arts. A non-volatile herbicide composition has the advantage of not evolving, or evolving to a reduced degree, through the air, to inadvertently contact desired plant growth. In practical effect, this advantageous property allows the herbicide compositions of the invention to be applied to undesired plant growth in greater strength or in closer proximity to desired above-ground plant growth.

The herbicide compositions can be used for both immediate and long-term control of a large variety of vegetation including those usually found in agricultural fields such as bushes, scrub brush, vines, and other weeds.

Illustrative of vegetation that can be controlled by these methods, depending significantly on the identity of the active herbicide compound, are: black mustard (*brassica nigra*), curly dock (*rumex crispus*), common groundsel (*senecio vulgaris*), pineapple weed (*matricaria matricarioides*), swamp smartweed (*kelp*) (*polygonum coccineum*), prickly lettus (*lactuca scariola*), lance-leaved groundcherry (*physalis lanceifolia*), annual sowthistle (*sonchus oleraceus*), london rocket (*sisymbrium irio*), common fiddleneck (*amsinckia intermedia*), hairy nightshade (*solanum sarrachoides*), shepherd's purse (*capsella bursa-pastoris*), sunflower (*helianthus annus*), common knotweed (*polygonum aviculare*), green amaranth (*amaranthus hybridus*), mare's tail (*conyza canadensis*), henbit (*lamium amplexicaule*), cocklebur (*xanthium strumarium*), cheeseweed (*malva parviflora*), lambsquarters (*chenopodium album*), puncture vine (*tribulus terrestris*) common purslane (*portulaca oleracea*), prostrate spurge (*euphorbia supina*), telegraph plant (*heterotheca grandiflora*), carpetweed (*mollugo verticillata*), yellow starthistle (*centaurea solstitialis*), milk thistle (*silybum marianum*), mayweed (*anthemis cotula*), burning nettle (*urtica urens*), fathen (*atriplex patula*), chickweed (*stellaria media*), scarlet pimpernel (*anagallis arvensis*) redroot pigweed (*amaranthus retroflexus*), minnerslettuce (*montia perfoliata*), turkey mullein (*eremocarpus setigerus*), nettleleaf goosefoot (*chenopodium murale*), prostrate pigweed (*amaranthus blitoides*), silverleaf nightshade (*solanum elaeagnifolium*), hoary cress (*cardaria draba*), largeseed dodder (*cuscuta indecora*), California burclover (*medicago polymorpha*), horse purslane (*trianthema portulacastrum*), field bindweed (*Iconvolvulus arvensis*), Russian knapweed (*centaurea repens*), flax-leaved fleabane (*conyza bonariensis*), wild radish (*raphanus sativus*), tumble pigweed (*amaranthus albus*), stephanomeria (*stephanomeria exigua*), wild turnip (*brassica campestris*), buffalo goard (*cucurbita foetidissima*), common mullein (*verbascum thapsus*), dandelion (*taraxacum officinale*), Spanish thistle (*xanthium spinosum*), chicory (*cichorium intybus*), sweet anise (*foeniculum vulgare*), annual yellow sweetclover (*melilotus indica*), poison hemlock (*conium maculatum*), broadleaf filaree (*erodium botrys*), whitestem filaree (*erodium moschatum*), redstem filaree (*erodium cicutarium*), ivyleaf morning-glory (*ipomea hederacea*), shortpod mustard (*brassica geniculata*), buckhorn plantain (*plantago lacenolata*), sticky chickweed (*cerastium viscosum*), himalaya blackberry (*rubus procerus*), purslane speedwell (*veronica peregrina*), Mexican tea (*chenopodium ambrosioides*), Spanish clover (*lotus purshianus*), Australian brassbuttons (*cotula australis*), goldenrod (*solidago californica*), citron (*citrullus lanatus*), hedge mustard (*sisymbrium orientale*), black nightshade (*solanum nodiflorum*), Chinese thornapple (*datura ferox*), bristly ox tongue (*picris echioides*), bull thistle (*cirsium vulgare*), spiny sowthistle (*sonchus asper*), Tasmanian goosefoot (*chenopodium pumilio*), goosefoot (*chenopodium botrys*), wright groundcherry (*physalis acutifolia*), tomatillo groundcherry (*physalis philadelphica*), pretty spurge (*euphorbia peplus*), bitter apple (*cucumis myriocarpus*), indian tobacco (*nicotiana bigelovii*), common morning-glory (*ipomoea purpurea*), waterplantain (*alisma triviale*), smartweed (*polygonum lapathifolium*), mature sowthistle (*sonchus asper*), yellow nutsedge (*cyperus esculentus*), purple nutsedge (*cyperus rotundus*), lupine (*lupinus formosus*), and grasses of the family Gramineae such as annual rye grass, blue grass, water grass, barnyard grass, bermuda grass, fescue, mat grass, Johnson grass, and the like.

The ingredients of a herbicide composition, e.g., one or more of the herbicide compound, surfactant, acidifying agent, etc., can be selected in view of the type of control desired (i.e., pre-emergent or post-emergent) and the type of vegetation to be controlled according to the known attributes of the herbicide compound.

As mentioned, other herbicides or herbicide compositions can optionally be added to herbicide compositions of the invention, to provide broad range protection against certain varieties of plants. As a single example, glyphosate acid (N-phosphonomethylglycine acid) can be useful in combination with other herbicide compounds in the herbicide compositions of the invention. Glyphosate acid can be included in a herbicide composition in any useful amount, especially in a herbicide application composition in an amount of glyphosate acid that will provide complementary protection to another herbicide compound of the herbicide composition. Imidazolinone acid herbicide compounds can also be used in combination with other active herbicide compounds. See, e.g., Applicants' copending Patent Application entitled "Herbicide Compounds Comprising Suspension Concentrate with Glyphosate Acid, Methods of Preparation, and Methods of Use," having U.S. Ser. No. 10/103,493; and Applicants' U.S. Pat. No. 6,703,346, entitled "Herbicide Compositions Comprising Imidazolinone Acid, Methods of Preparation, and Methods of Use," incorporated herein by reference. Also, the pH of such a herbicide composition can preferably be below the pH of glyphosate acid or imidazolinone acid, as relevant, e.g., below about 2.6, so the glyphosate or imidazolinone can exist in the acid form, preferably improving efficacy and avoiding precipitation.

EXAMPLES

Below are described specific microemulsion-forming-concentrates of acid herbicides in surfactants, diluted to form microemulsions (all amounts in weight percent).

| 2,4D Acid ME Attempt to make 33.3%/wt 2,4-D. Formed an initial clear MFC which was diluted to 2% in water to form a microemulsion. Formulation crystallized in 24 hours. | |
|---|---|
| Tomadol 1-5 | 32.2% |
| Tomadol 1-7 | 32.8 |
| Rhodafac RS 710 | 1.0 |
| 98% 2,4D Acid | 34.0 |

2% dilution (2 parts MFC to 98 parts water) in 342 ppm is clear microemulsion, 4 hrs.

| 2,4D Acid ME | |
|---|---|
| Tomadol 1-5 | 36.1% |
| Tomadol 1-7 | 36.1 |
| 98% 2,4D Acid | 27.8 |

2% dilution in 342 ppm is clear microemulsion, 4 hrs.

| Fluroxypyr acid & 2,4-D Acid ME | | |
|---|---|---|
| Tomadol 1-5 | 13.9% | |
| Tomadol 1-7 | 13.9 | |
| SAG 10 AF | 0.1 | |
| Trymeen 6607 | 50.0 | Cognis tallow amine ethoxylate |
| 99% Fluroxypyr Acid | 11.0 | |
| 98% 2,4D Acid | 11.1 | |

2% dilution in 342 ppm opaque microemulsion @ 4 hrs

| 2,4D Acid ME | | |
|---|---|---|
| Surfonic L12-6 | 71.3% | Huntsman 12 carbon 6 mole linear alcohol |
| SAG 10 AF | 0.1 | |
| 98% 2,4D Acid | 28.6 | |

% dilution in 342 ppm is opaque microemulsion

2,4D Acid ME

| | | |
|---|---|---|
| Tomadol 1-5 | 63.2% | |
| Stepfac 8170 | 8.0 | Stepan Phosphoric acid ester |
| SAG 10 AF | 0.1 | |
| 98% 2,4D Acid | 28.6 | |

5% dilution in 342 ppm is opaque microemulsion

2,4D Acid ME

| | | |
|---|---|---|
| Surfonic L12-6 | 63.3% | |
| Surfonic PE-1218 | 8.0 | Huntsman Phosphoric acid ester |
| SAG 10 AF | 0.1 | |
| 98% 2,4D Acid | 28.6 | |

% dilution in 342 ppm is opaque microemulsion

2,4D Acid ME

| | | |
|---|---|---|
| Surfonic L12-6 | 61.3% | Huntsman linear alcohol |
| Surfonic PE-1218 | 10.0 | Huntsman Phosphoric acid ester |
| SAG 10 AF | 0.1 | |
| 98% 2,4D Acid | 28.6 | |

2% dilution in 342 ppm is opaque microemulsion

2,4D Acid ME

| | | |
|---|---|---|
| Surfonic DDA6 | 61.3% | Huntsman branched alcohol ethoxylate |
| Surfonic PE-1218 | 10.0 | Huntsman Phosphoric acid ester |
| SAG 10 AF | 0.1 | |
| 98% 2,4D Acid | 28.6 | |

2% dilution in 342 ppm is opaque microemulsion

2,4D Acid ME

| | | |
|---|---|---|
| Surfonic TDA6 | 63.3% | Huntsman tridecyl alcohol ethoxylate |
| Surfonic PE-1218 | 8.0 | Huntsman Phosphoric acid ester |
| SAG 10 AF | 0.1 | |
| 98% 2,4D Acid | 28.6 | |

2% dilution in 342 ppm is opaque microemulsion

2,4D Acid ME

| | | |
|---|---|---|
| Tomadol 1-5 | 32.0 | Tomah linear alcohol ethoxylates |
| Tomadol 1-7 | 31.30 | |
| Stepfac 8170 | 8.00 | Stepan Phosphoric acid ester |
| SAG 10 AF | 0.1 | |
| 98% 2,4D Acid | 28.6 | |

% dilution in 342 ppm is opaque microemulsion

2,4D Acid ME

| | | |
|---|---|---|
| Tomadol 1-5 | 32.0 | Tomah linear alcohol ethoxylates |
| Tomadol 1-7 | 31.30 | |
| Stepfac 8170 | 8.00 | Stepan Phosphoric acid ester |

-continued

2,4D Acid ME

| | |
|---|---|
| SAG 10 AF | 0.1 |
| 98% 2,4D Acid | 28.6 |

2% dilution in 342 ppm is opaque microemulsion

Fluazifop Acid ME

| | | |
|---|---|---|
| Surfonic L12-6 | 63.3% | |
| Stepfac 8170 | 8.00 | Stepan Phosphoric acid ester |
| SAG 10 AF | 0.10 | |
| 90% Fluzafop Acid | 28.60 | |

Fluroxypyr Acid ME, using organic solvent

| | | |
|---|---|---|
| Surfonic L12-6 | 24%/wt | linear alcohol nonionic |
| Surfonic T-15 | 45 | tallow amine cationic |
| THFA # | 10 | Solvent |
| 99% fluroxypyr acid | 21 | Active | tetrahydrofurfuryl alcohol

2,4D Acid ME

| | | |
|---|---|---|
| Surfonic OP-70 | 63.3% | 7 mole octyl phenol |
| Stepfac 8170 | 8.0 | |
| 98% Dow 2,4D Acid | 28.6 | |
| SAG 10 Antifoam | 0.1 | |

2,4D Acid ME

| | | |
|---|---|---|
| Tergitol NP6 | 63.3% | 6 mole nonyl phenol |
| Stepfac 8170 | 8.0 | |
| 98% Dow 2,4D Acid | 28.6 | |
| SAG 10 Antifoam | 0.1 | |

2,4D Acid ME

| | | |
|---|---|---|
| Trylox 5902 | 63.3% | 16 mole castor oil ethoxylate |
| Stepfac 8170 | 8.0 | |
| 98% Dow 2,4D Acid | 28.6 | |
| SAG 10 Antifoam | 0.1 | |

2,4D Acid ME

| | | |
|---|---|---|
| Span 20 | 35.3% | sorbitan laurate |
| Tween 80 | 28.0 | polysorbate 80 |
| Stepfac 8170 | 8.0 | |
| 98% Dow 2,4D Acid | 28.6 | |
| SAG 10 Antifoam | 0.1 | |

| 2,4D Acid ME | | |
|---|---|---|
| Sophroflor 796P | 68.3% | ethoxylated tristerylphenol |
| Stepfac 8170 | 8.0 | |
| 98% Dow 2,4D Acid | 28.6 | |
| SAG 10 Antifoam | 0.1 | |

| ME with Glyphosate Acid & 2,4D Acid | |
|---|---|
| Dipropylene glycol mono methyl ester | 5.00% |
| 40 mole castor oil ethoxylate | 10.00 |
| 98% 2,4D acid | 6.20 |
| 97% glyphosate acid | 6.20 |
| Amads | 72.50 |
| Antifoam | 0.10 |

Microemulsions were formed as follows:

Microemulsion-forming-concentrate was formed by adding dicamba to surfactant and mixing until dissolved with heat. Then, Engame and antifoam were mixed and added to the dicamba/surfactant MFC to form a microemulsion:

| | | |
|---|---|---|
| Neodol 1-5 | 20.00% | linear alcohol ethoxylate |
| 88% dicamba acid | 6.60 | |
| Engame | 73.30 | |
| Antifoam | 0.10 | |

(Engame is 9.6% glyphosate acid dissolved in a urea-sulfuric acid water base.)

In a method of using a composition containing herbicide acid (the combination of glyphosate acid and 2,4-D acid), surfactant, and acidifying agent, glyphosate acid was dissolved in surfactant and ingredients to produce a sulfuric acid/urea adduct, and that mixture was then used to solubilize 2,4-D in surfactant.

A. Vessel—Add in Order Listed Keeping Temperature Below 130° F.

| | | |
|---|---|---|
| Water | 13.17% | |
| 93% sulfuric acid | 35.30 | |
| 97% glyphosate acid | 6.80 | |
| Urea | .30 | |
| Copper sulfate | 0.02 | corrosion inhibitor |
| Antifoam | 0.01 | |

B. Vessel—Add in Order Listed Keeping Temperature Between 130-150° F.

| | | |
|---|---|---|
| Tomadol 1-5 | 8.00 | 11 carbon 5 mole linear alcohol ethoxylate |
| Tomadol 1-7 | 8.00 | 11 carbon 7 mole linear alcohol ethoxylate |
| Rhodofac RS 710 | 1.70 | anionic, phosphate ester surfactant |
| 98% 2,4D Acid | 6.70 | |

The samples were clear. The solution of Vessel B was a microemulsion. Adding the solution of Vessel A to the solution of Vessel B with agitation formed a clear MFC product which when diluted, 2 parts MFC product to 98 parts water, formed an opaque microemulsion.

A suspension concentrate comprising 3 lbs. glyphosate acid per gallon can be prepared as described above, with ingredients as follows:

| | | |
|---|---|---|
| Water | 41.60% | |
| SAG 30 Antifoam | 0.30 | |
| Propylene Glycol | 5.00 | |
| Surfonic T-15 | 8.00 | tallow amine 15 mole |
| 86% glyphosate we | 36.10 | wet cake |
| Tersperse 4984 | 2.00 | dispersant, wetter |
| 2% Kelzan 0.5% Proxel | 7.00 | |

Other exemplary suspension concentrate formulations can include a higher amount of surfactant (e.g., 8%) and can have a glyphosate acid concentration of 4 pounds per gallon, as follows:

| | | |
|---|---|---|
| Water | 32.45% | |
| SAG 30 | 0.30 | anti foam |
| Propylene Glycol | 8.00 | antifreeze |
| AU-392 | 8.00 | nonionic/tallow amine blend |
| Glyphosate WC, Dow | 45.30 | active, 39.0% glyphosate acid |
| Tersperse 4894 | 2.00 | dispersant, wetter |
| 2% Kelzan-0.5% Proxel | 4.00 | thickener & antimicrobial |
| Total | 100.00 | |

Glyphosate Acid Content of this Formulation:
39.0% w/w
480 g/L
4.0 lb/gal

| | | |
|---|---|---|
| Water | 32.45% | |
| SAG 30 | 0.30 | anti foam |
| Propylene Glycol | 8.00 | antifreeze |
| LI-700 | 8.00 | lecithin derivative |
| Glyphosate WC, Dow | 45.30 | active, 39.0% glyphosate acid |
| Tersperse 2500 | 2.00 | dispersant |
| % Kelzan-0.5% Proxel | 4.00 | thickener & antimicrobial |
| Total | 100.00 | |

Examples 1-5

Materials and Methods

Five experiments were conducted to evaluate the efficacy of a variety of different types of herbicide formulations, including formulations from suspension concentrates, and to evaluate the effect of adding acids to the spray solution as an adjuvant (see Tables 1-5). Each treatment in the experiment was replicated three times. An untreated control was also included in each experiment.

Experiment one was designed to identify useful acid concentrations of four acids when used with a 2,4-D acid (2,4-dichlorophenoxy acetic acid) formulation (PCC-1133), or a glyphosate (N-(phosphonomethyl)glycine) acid formulation (PCC-1168 suspension concentrate containing glyphosate acid), in a greenhouse. These treatments were compared to standard 2,4-D and glyphosate formulations (ROUNDUP ULTRA, SABER, SALVO), and an untreated control.

Experiment two determined the effect of adding four different acid adjuvants to five formulations of glyphosate: RODEO, ROUNDUP, ROUNDUP ULTRA, ENGAME, and PCC-1168, at four different glyphosate rates. (The Kochia for experiment 2 did not germinate well.)

Experiment three considered the effect of adding acid adjuvants to PCC-1133, and compared the results to SALVO, SABER, and PCC-1133. Experiment four determined the effect of a variety of acid adjuvants: sulfuric acid, hydrochloric acid, nitric acid, glacial acetic acid, phosphoric acid, perchloric acid, perchloric acid, and polyphosphoric acid, on the efficacy of the 2,4-D acid formulation, PCC-1133, and the acid formulation alone, compared to ester and amine formulations of 2,4-D.

Experiment four determined the effect of a variety of acid adjuvants: sulfuric acid, hydrochloric acid, nitric acid, glacial acetic acid, phosphoric acid, perchloric acid, perchloric acid, and polyphosphoric acid, on the efficacy of the 2,4-D acid formulation, PCC-1133.

Experiment five determined the effect of the same acid adjuvants on the efficacy of the glyphosate acid formulation, PCC-1168, compared to another glyphosate formulation, Rodeo.

PCC-1168 Suspension Concentrate Formulation

| INGREDIENT | % AI-Tech | %/WT |
|---|---|---|
| Water | | 44.60 |
| SAG 30, OSI, Antifoam | | 0.30 |
| Proplyene Glycol, Antifreeze | | 8.00 |
| Surfonic L12-6, Huntsman, nonionic wetting agent | | 0.50 |
| Glyphosate WC, Dow, Active Ingredient | 86.00 | 36.10 |
| Tersperse 4894, Huntsman, nonionic dispersant | | 3.50 |
| Gum 2% Kelzan-0.5% Proxel Premix*, thickener & antimicrobial | | 7.00 |
| Add in order listed to cowles high speed mixer stopping prior to Kelzan-Proxel addition | | |
| Grind to 5-18 microns, 4 hrs in attritor, 60% | | |
| Let down to mix tank with scales | TOTAL | 100.00 |
| Add calculated amount Kelzan/Proxel Premix** | | |
| Add to milled liquid. Blend moderately for 30 min. | | |

(*Delivers 0.14% Kelzan, 0.03% Proxel)

PCC-1133 Microemulsion Formulation

| 2,4-D Acid | 28.0 | 98% 2,4-D acid technical flake |
|---|---|---|
| Tomadol 1-5 | 32.0 | 11 carbon 5 mole linear alcohol ethoxylate |
| Tomadol 1-7 | 32.3 | 11 carbon 7 mole linear alcohol ethoxylate |
| Rhodofac RS 710 | 8.0 | anionic, phosphate ester surfactant |
| SAG 10 Antifoam | 0.1 | |

The PCC-1133 microemulsion was prepared by adding surfactants to a mixing vessel and warming to 130E-150 F. Antifoam and acid were added and mixed in until clear, with the 2,4-D acid becoming dissolved in the surfactant, producing a MFC. A microemulsion was formed from the MFC by combining 2 ml of the MFC with 98 ml water with agitation.

Procedure

For each experiment conducted, greenhouse flats 26 cm2 by 6 cm deep were filled with Metro Mix 200 potting soil (experiments one and two) or Metro Mix 350 (experiments three, four, and five). The soil was pre-wetted before filling the flats. Six furrows were pressed into the soil in each flat using a custom designed form. Corn, tame oats, wheat, pinto beans, cotton, and sunflower were planted in each tray. Cottonseed was soaked for three days previous to planting to improve germination. However, germination was still unacceptable and kochia was substituted in experiments two through five. One species was planted in each of the six rows in each flat. Five seeds were planted in each row of corn, bean, and cotton, and sunflower. Six seeds were planted in each row of oat and wheat. Kochia was sprinkled evenly along the row by hand. Each flat was covered with 2 cm of soil and placed in the greenhouse. Greenhouse conditions were 28/20 C day/night temperatures and 16/8 h day night periods. Light was supplemented with 400 W sodium halide lights.

The plants were allowed to germinate and grow in the greenhouse for 2 weeks and then treated. Treatments were mixed using serial dilutions. In experiment one, the percent acid was reduced in each dilution by one half. In experiments 2 through 5 each dilution reduced the herbicide rate by one half. Acid concentrations were calculated and mixed so that a treatment with one of the acids or LI-136 would have the same amount of acid as the treatment with PCC-1174 (see infra). Therefore, a treatment designated 4% sulfuric acid would have the same amount of acid as a treatment with 4% PCC-1174.

After mixing in experiments one, four, and five, the pH of the spray solution of each treatment was measured with a, VWR Scientific model 8005 pH meter. The pH was measured to determine if the acid used or the amount of acid added was sufficient to lower the pH below the pKa of the acid herbicides used. The pKa of 2,4-D acid in the PCC-1133 is 2.87. The pKa of glyphosate acid in PCC-1168 is about 2.5 or 2.6.

At the time of treatment, crops were at the following stages: corn-2 to 3 1f, oat-2 to 3 1f, cotton-cotyledon, kochia-7 1f, bean-1st trifoliate, and sunflower-2 to 4 1f. Plants were treated using a greenhouse track sprayer equipped with an 8001 E nozzle and calibrated to deliver 140 L ha-1 at the height of the crop canopy. Each treatment was simultaneously applied to three trays of plants, one for each replicate. After treatment, the plants were left in the head house to dry and then transferred to the greenhouse. Plants in each treatment were evaluated visually for injury 1 day, 1 week, and 2 weeks after treatment.

Summary of Variables of Experiments 1-5

Experiment 1

| Acid Treatment | Acid of each Volume v/v % | Herbicide | Herbicide Rate lb/A | Plants | Reps |
|---|---|---|---|---|---|
| PCC-1174 | 0 | PCC-1133 | 0.125 | dry beans | 3 |
| Sulfuric | 0.125 | PCC-1168 | 0.125 | wheat | 2 of standards |
| Phosphoric | 0.5 | Roundup Ultra | 0.125 | cotton | 2 of PCC-1133 and 1168 alone |
| L1-136 | 1 | Saber | 0.125 | corn | =192 flats |
| | 2 | Salvo | 0.125 | sunflower | |
| | 4 | Untreated | 0.125 | oats | |

Experiment 2

| Treatment | Rates lb/A | Plants | Reps |
|---|---|---|---|
| Rodeo | 0.0313 | dry beans | 3 |
| Roundup | 0.0625 | wheat | |
| Ultra | 0.125 | kochia | |
| | | (did not germinate) | |
| Engame | 0.25 | corn | |
| PCC-1168 | | sunflower | |
| PCC-1168 + PCC-1174 (4%) | | oats | |
| PCC-1168 + sulfuric (2%) | | | |
| PCC-1168 + phosphoric (2%) | | | |
| PCC-1168 + LI-136 (2%) | | | |

Experiment 3

| Treatment | rates lb/A | Plants | Reps |
|---|---|---|---|
| SALVO | 0.0313 | dry beans | 3 |
| SABER | 0.0625 | wheat | |
| PCC-1133 | 0.125 | kochia | |
| PCC-1133 + PCC-1174 (2%) | 0.025 | corn | |
| PCC-1133 + Sulfuric (2%) | 0.5 | sunflower | |
| PCC-1133 + Phosphoric (2%) | | oats | |
| PCC-1133 + LI-136 (2%) | | | |

Experiment 4

| Treatment | rates lb/A | Plants | Reps |
|---|---|---|---|
| PCC-1133 | 0.0313 | dry beans | 3 |
| PCC-1133 + Sulfuric (2%) | 0.0625 | wheat | |
| PCC-1133 + HCl (2%) | 0.125 | kochia | |
| PCC-1133 + Nitric (2%) | 0.025 | corn | |
| PCC-1133 + Acetic (2%) | 0.5 | sunflower | |
| PCC-1133 + Phosphoric (2%) | | oats | |
| PCC-1133 + Perchloric (2%) | | | |
| PCC-1133 + Polyphosphoric (2%) | | | |

Experiment 5

| Treatment | rates lb/A | Plants | Reps |
|---|---|---|---|
| PCC-1168 | 0.0313 | dry beans | 3 |
| PCC-1168 + Sulfuric (4%) | 0.0625 | wheat | |
| PCC-1168 + HCl (4%) | 0.125 | kochia | |
| PCC-1168 + Nitric (4%) | 0.025 | corn | |
| PCC-1168 + Acetic (4%) | 0.5 | sunflower | |
| PCC-1168 + Phosphoric (4%) | | oats | |
| PCC-1168 + Perchloric (4%) | | | |
| PCC-1168 + Polyphosphoric (4%) | | | |

Following are data that illustrate the efficacy of various herbicide compositions of Experiments 2-5. The injury caused by the herbicide treatment was rated visually. Plants were observed and compared to the untreated control. All the plants of each species in each replication were given a single rating. A rating of 0=no injury—the plants look the same as the untreated. A rating of 100=dead—usually highly necrotic, brown and no chance of producing seed.

SALVO® is a commercially available product of Platte Chemical Co. containing 5 lb 2,4-D acid equivalent/gallon as 2-ethyl-hexyl ester of 2,4-D SABER® is 2,4-D formulated as a dimethylamine salt (2,4-dichlorophenoxy dimethylamine salt), i.e., is a commercially available product of Platte Chemical Company containing 3.8 lb 2,4-D acid equivalent/gallon as dimethylamine salt.

RODEO is a soluble liquid water-based formulation of IPA, glyphosate, and water, commercially available from MONSANTO, and was used according to the labeling instructions.

RODEO ULTRA is a glyphosate salt herbicide composition commercially available from MONSANTO, and was used according to the labeling instructions.

ENGAME is a soluble liquid water-based formulation of glyphosate acid, urea, sulfuric acid, and water, commercially available from ENTEK, and was used according to the labeling instructions.

ROUNDUP and ROUNDUP ULTRA are commercially available IPA glyphosate salt and surfactant herbicide compositions.

Acidifying Agents 20 HCl 37%

Nitric 70%

Glacial Acetic 100%

Perchloric 60%

Polyphosphoric 100%

PCC-1174
Commercially available as "AMADS," which is urea and H2SO4 in water:

| Chemical Name | I-amino methanamide dihydrogen tetraoxosulfate, or sulfuric acid and urea |
|---|---|
| Molecular Formula | $NH_2C(OH)NHSO_4H_2$ |

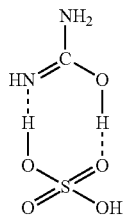

| INGREDIENT | %/WT |
|---|---|
| Water | 22.99 |
| 93% Sulfuric Acid | 48.65 |
| 99% Urea | 26.64 |
| Stepfac 8170 | 1.71 |
| SAG 10 Antifoam | 0.01 |

LI-136=LI-136 is a blend of 50 wt. % 21-0-0 urea liquor and 50 wt percent of 72% phosphoric acid in water. The phrase "21-0-0 urea liquor" means a liquid that contains 21% by volume urea 10 (nitrogen), 0% by volume phosphate (phosphorus), and 0% by volume potash (potassium).

Each of these acids were used as is and combined with the PCC-1133 or PCC-1168 to form a solution that contains 2 percent or 4 percent by volume of the acid solution, as indicated in the data tables, and such that the pH of the herbicide composition was below the pKa of the particular herbicide compound.

The ingredients of the herbicide compositions as applied are listed in the following data tables for Experiments 2-5, and were diluted with water and used at the rates indicated for herbicide ingredients and acidifying agents.

| DATA FOR EXPERIMENT 2 (TWO WEEK) | | | | | | | |
|---|---|---|---|---|---|---|---|
| | | Rate | Units | corn | tame oat | spring wheat | dry bean | sunflower |
| 1 | RODEO | .0313 | LB AE/A | 0.0 | 0.0 | 0.0 | 0.0 | 0.0 |
| 2 | RODEO | .0625 | LB AE/A | 0.0 | 0.0 | 0.0 | 5.0 | 5.0 |
| 3 | RODEO | 0.125 | LB AE/A | 20.0 | 20.0 | 0.0 | 30.0 | 40.0 |
| 4 | RODEO | 0.25 | LB AE/A | 30.0 | 10.0 | 40.0 | 60.0 | 100.0 |
| 5 | ROUNDUP | .0313 | LB AE/A | 0.0 | 0.0 | 0.0 | 0.0 | 0.0 |
| 6 | ROUNDUP | .0625 | LB AE/A | 20.0 | 5.0 | 0.0 | 33.3 | 40.0 |
| 7 | ROUNDUP | 0.125 | LB AE/A | 70.0 | 70.0 | 60.0 | 50.0 | 90.0 |
| 8 | ROUNDUP | 0.25 | LB AE/A | 90.0 | 80.0 | 70.0 | 80.0 | 100.0 |
| 9 | ROUNDUP ULTRA | .0313 | LB AE/A | 20.0 | 0.0 | 0.0 | 0.0 | 0.0 |
| 10 | ROUNDUP ULTRA | .0625 | LB AE/A | 30.0 | 20.0 | 40.0 | 50.0 | 40.0 |
| 11 | ROUNDUP ULTRA | 0.125 | LB AE/A | 90.0 | 49.0 | 70.0 | 70.0 | 90.0 |
| 12 | ROUNDUP ULTRA | 0.25 | LB AE/A | 100.0 | 80.0 | 90.0 | 80.0 | 100.0 |
| 13 | ENGAME | .0313 | LB AE/A | 20.0 | 0.0 | 0.0 | 60.0 | 60.0 |
| 14 | ENGAME | .0625 | LB AE/A | 40.0 | 20.0 | 20.0 | 60.0 | 63.3 |
| 15 | ENGAME | 0.125 | LB AE/A | 50.0 | 40.0 | 30.0 | 60.0 | 90.0 |
| 16 | ENGAME | 0.25 | LB AE/A | 90.0 | 80.0 | 90.0 | 75.0 | 100.0 |
| 17 | PCC-1168 | .0313 | LB AE/A | 0.0 | 0.0 | 0.0 | 0.0 | 0.0 |
| 18 | PCC-1168 | .0625 | LB AE/A | 0.0 | 0.0 | 0.0 | 0.0 | 0.0 |
| 19 | PCC-1168 | 0.125 | LB AE/A | 20.0 | 50.0 | 10.0 | 20.0 | 16.7 |
| 20 | PCC-1168 | 0.25 | LB AE/A | 70.0 | 60.0 | 80.0 | 46.7 | 40.0 |
| 21 | PCC-1168 PCC-1174 | .0313 4 | LB AE/A % V/V | 50.0 | 30.0 | 5.0 | 40.0 | 40.0 |
| 22 | PCC-1168 PCC-1174 | .0625 4 | LB AE/A % V/V | 50.0 | 60.0 | 20.0 | 40.0 | 40.0 |
| 23 | PCC-1168 PCC-1174 | 0.125 4 | LB AE/A % V/V | 70.0 | 60.0 | 70.0 | 63.3 | 76.7 |
| 24 | PCC-1168 PCC-1174 | 0.25 4 | LB AE/A % V/V | 90.0 | 80.0 | 80.0 | 80.0 | 100.0 |
| 25 | PCC-1168 SULFURIC ACID | .0313 2 | LB AE/A % V/V | 10.0 | 10.0 | 10.0 | 40.0 | 5.0 |
| 26 | PCC-1168 SULFURIC ACID | .0625 2 | LB AE/A % V/V | 10.0 | 10.0 | 10.0 | 40.0 | 10.0 |
| 27 | PCC-1168 SULFURIC ACID | 0.125 2 | LB AE/A % V/V | 50.0 | 20.0 | 10.0 | 60.0 | 28.0 |
| 28 | PCC-1168 SULFURIC ACID | 0.25 2 | LB AE/A % V/V | 90.0 | 70.0 | 80.0 | 80.0 | 90.0 |
| 29 | PCC-1168 PHOSPHORIC ACID | .0313 4 | LB AE/A % V/V | 0.0 | 0.0 | 0.0 | 0.0 | 1.7 |
| 30 | PCC-1168 PHOSPHORIC ACID | .0625 4 | LB AE/A % V/V | 0.0 | 0.0 | 0.0 | 20.0 | 5.0 |
| 31 | PCC-1168 PHOSPHORIC ACID | 0.125 4 | LB AE/A % V/V | 5.0 | 5.0 | 5.0 | 40.0 | 40.0 |
| 32 | PCC-1168 PHOSPHORIC ACID | 0.25 4 | LB AE/A % V/V | 60.0 | 60.0 | 40.0 | 60.0 | 80.0 |
| 33 | PCC-1168 LI-136 | .0313 4 | LB AE/A % V/V | 5.0 | 0.0 | 0.0 | 10.0 | 20.0 |
| 34 | PCC-1168 L1-136 | .0625 4 | LB AE/A % V/V | 5.0 | 0.0 | 0.0 | 20.0 | 40.0 |
| 35 | PCC-1168 LI-136 | 0.125 4 | LB AE/A % V/V | 20.0 | 0.0 | 10.0 | 40.0 | 70.0 |
| 36 | PCC-1168 L1-136 | 0.25 4 | LB AE/A % V/V | 50.0 | 50.0 | 60.0 | 70.0 | 100.0 |
| 37 | UNTREATED | | | 0.0 | 0.0 | 0.0 | 0.0 | 0.0 |

| DATA FOR EXPERIMENT 3 (TWO WEEK) | | | | | | | |
|---|---|---|---|---|---|---|---|
| | | Rate | Units | corn | tame oat | *kochia* | winter wheat | dry bean | sunflower |
| 1 | SALVO | .0313 | LB AE/A | 0.0 | 0.0 | 0.0 | 0.0 | 10.0 | 10.0 |
| 2 | SALVO | .0625 | LB AE/A | 0.0 | 0.0 | 0.0 | 0.0 | 30.0 | 30.0 |
| 3 | SALVO | 0.125 | LB AE/A | 0.0 | 0.0 | 0.0 | 0.0 | 60.0 | 40.0 |
| 4 | SALVO | 0.25 | LB AE/A | 0.0 | 0.0 | 0.0 | 0.0 | 90.0 | 90.0 |
| 5 | SALVO | 0.5 | LB AE/A | 0.0 | 0.0 | 0.0 | 0.0 | 90.0 | 90.0 |
| 6 | SABER | .0313 | LB AE/A | 0.0 | 0.0 | 0.0 | 0.0 | 5.0 | 0.0 |
| 7 | SABER | .0625 | LB AE/A | 0.0 | 0.0 | 0.0 | 0.0 | 10.0 | 5.0 |
| 8 | SABER | 0.125 | LB AE/A | 0.0 | 0.0 | 0.0 | 0.0 | 50.0 | 30.0 |
| 9 | SABER | 0.25 | LB AE/A | 0.0 | 0.0 | 0.0 | 0.0 | 80.0 | 70.0 |
| 10 | SABER | 0.5 | LB AE/A | 0.0 | 0.0 | 0.0 | 0.0 | 90.0 | 85.0 |
| 11 | PCC-1133 | .0313 | LB AE/A | 0.0 | 0.0 | 0.0 | 0.0 | 20.0 | 10.0 |
| 12 | PCC-1133 | .0625 | LB AE/A | 0.0 | 0.0 | 0.0 | 0.0 | 30.0 | 20.0 |
| 13 | PCC-1133 | 0.125 | LB AE/A | 0.0 | 0.0 | 0.0 | 0.0 | 50.0 | 50.0 |

| | | Rate | Units | corn | tame oat | *kochia* | winter wheat | dry bean | sunflower |
|---|---|---|---|---|---|---|---|---|---|
| | DATA FOR EXPERIMENT 3 (TWO WEEK) | | | | | | | | |
| 14 | PCC-1133 | 0.25 | LB AE/A | 0.0 | 0.0 | 0.0 | 0.0 | 85.0 | 80.0 |
| 15 | PCC-1133 | 0.5 | LB AE/A | 0.0 | 0.0 | 0.0 | 0.0 | 90.0 | 90.0 |
| 16 | PCC-1133 PCC-1174 | .0313 2 | LB AE/A % V/V | 0.0 | 0.0 | 0.0 | 0.0 | 50.0 | 15.0 |
| 17 | PCC-1133 PCC-1174 | .0625 2 | LB AE/A % V/V | 0.0 | 0.0 | 0.0 | 0.0 | 50.0 | 30.0 |
| 18 | PCC-1133 PCC-1174 | 0.125 2 | LB AE/A % V/V | 0.0 | 0.0 | 0.0 | 0.0 | 70.0 | 60.0 |
| 19 | PCC-1133 PCC-1174 | 0.25 2 | LB AE/A % V/V | 0.0 | 0.0 | 0.0 | 0.0 | 95.0 | 95.0 |
| 20 | PCC-1133 PCC-1174 | 0.5 2 | LB AE/A % V/V | 0.0 | 0.0 | 0.0 | 0.0 | 98.0 | 95.0 |
| 21 | PCC-1133 SULFURIC ACID | .0313 2 | LB AE/A % V/V | 0.0 | 0.0 | 0.0 | 0.0 | 35.0 | 20.0 |
| 22 | PCC-1133 SULFURIC ACID | .0625 2 | LB AE/A % V/V | 0.0 | 0.0 | 0.0 | 0.0 | 40.0 | 30.0 |
| 23 | PCC-1133 SULFURIC ACID | 0.125 2 | LB AE/A % V/V | 0.0 | 0.0 | 0.0 | 0.0 | 70.0 | 60.0 |
| 24 | PCC-1133 SULFURIC ACID | 0.25 2 | LB AE/A % V/V | 0.0 | 0.0 | 0.0 | 0.0 | 95.0 | 90.0 |
| 25 | PCC-1133 SULFURIC ACID | 0.5 2 | LB AE/A % V/V | 0.0 | 0.0 | 0.0 | 0.0 | 98.0 | 98.0 |
| 26 | PCC-1133 PHOSPHORIC ACID | .0313 2 | LB AE/A % V/V | 0.0 | 0.0 | 0.0 | 0.0 | 30.0 | 30.0 |
| 27 | PCC-1133 PHOSPHORIC ACID | .0625 2 | LB AE/A % V/V | 0.0 | 0.0 | 0.0 | 0.0 | 40.0 | 30.0 |
| 28 | PCC-1133 PHOSPHORIC ACID | 0.125 2 | LB AE/A % V/V | 0.0 | 0.0 | 0.0 | 0.0 | 65.0 | 60.0 |
| 29 | PCC-1133 PHOSPHORIC ACID | 0.25 2 | LB AE/A % V/V | 0.0 | 0.0 | 0.0 | 0.0 | 90.0 | 90.0 |
| 30 | PCC-1133 PHOSPHORIC ACID | 0.5 2 | LB AE/A % V/V | 0.0 | 0.0 | 0.0 | 0.0 | 95.0 | 97.0 |
| 31 | PCC-1133 LI-136 | .0313 2 | LB AE/A % V/V | 0.0 | 0.0 | 0.0 | 0.0 | 28.3 | 10.0 |
| 32 | PCC-1133 LI-136 | .0625 2 | LB AE/A % V/V | 0.0 | 0.0 | 0.0 | 0.0 | 50.0 | 40.0 |
| 33 | PCC-1133 LI-136 | 0.125 2 | LB AE/A % V/V | 0.0 | 0.0 | 0.0 | 0.0 | 70.0 | 60.0 |
| 34 | PCC-1133 LI-136 | 0.25 2 | LB AE/A % V/V | 0.0 | 0.0 | 0.0 | 0.0 | 90.0 | 90.0 |
| 35 | PCC-1133 LI-136 | 0.5 2 | LB AE/A % V/V | 0.0 | 0.0 | 0.0 | 0.0 | 95.0 | 90.0 |
| 36 | UNTREATED | | | 0.0 | 0.0 | 0.0 | 0.0 | 0.0 | 0.0 |

| | | Rate | Units | Corn | Tame oat | *Kochia* | winter wheat | dry bean | sunflower |
|---|---|---|---|---|---|---|---|---|---|
| | DATA FOR EXPERIMENT 4 (ONE WEEK) | | | | | | | | |
| 1 | PCC-1133 | .0313 | LB AE/A | 0.0 | 0.0 | 0.0 | 0.0 | 7.0 | 7.0 |
| 2 | PCC-1133 | .0625 | LB AE/A | 0.0 | 0.0 | 0.0 | 0.0 | 30.0 | 20.0 |
| 3 | PCC-1133 | 0.125 | LB AE/A | 0.0 | 0.0 | 0.0 | 0.0 | 50.0 | 40.0 |
| 4 | PCC-1133 | 0.25 | LB AE/A | 0.0 | 0.0 | 0.0 | 0.0 | 60.0 | 60.0 |
| 5 | PCC-1133 | 0.5 | LB AE/A | 0.0 | 0.0 | 0.0 | 0.0 | 80.0 | 80.0 |
| 6 | PCC-1133 SULFURIC ACID | .0313 2 | LB AE/A % V/V | 0.0 | 0.0 | 0.0 | 0.0 | 30.0 | 40.0 |
| 7 | PCC-1133 SULFURIC ACID | .0625 2 | LB AE/A % V/V | 0.0 | 0.0 | 0.0 | 0.0 | 40.0 | 40.0 |
| 8 | PCC-1133 SULFURIC ACID | 0.125 2 | LB AE/A % V/V | 0.0 | 0.0 | 0.0 | 0.0 | 80.0 | 60.0 |
| 9 | PCC-1133 SULFURIC ACID | 0.25 2 | LB AE/A % V/V | 0.0 | 0.0 | 0.0 | 0.0 | 80.0 | 85.0 |
| 10 | PCC-1133 SULFURIC ACID | 0.5 2 | LB AE/A % V/V | 0.0 | 0.0 | 0.0 | 0.0 | 95.0 | 90.0 |
| 11 | PCC-1133 HYDROCHLORIC ACID | .0313 2 | LB AE/A % V/V | 0.0 | 0.0 | 0.0 | 0.0 | 60.0 | 50.0 |
| 12 | PCC-1133 HYDROCHLORIC ACID | .0625 2 | LB AE/A % V/V | 0.0 | 0.0 | 0.0 | 0.0 | 55.0 | 55.0 |
| 13 | PCC-1133 HYDROCHLORIC ACID | 0.125 2 | LB AE/A % V/V | 0.0 | 0.0 | 0.0 | 0.0 | 65.0 | 70.0 |
| 14 | PCC-1133 HYDROCHLORIC ACID | 0.25 2 | LB AE/A % V/V | 0.0 | 0.0 | 0.0 | 0.0 | 90.0 | 85.0 |

DATA FOR EXPERIMENT 4 (ONE WEEK)

| | | Rate | Units | Corn | Tame oat | *Kochia* | winter wheat | dry bean | sunflower |
|---|---|---|---|---|---|---|---|---|---|
| 15 | PCC-1133 | 0.5 | LB AE/A | 0.0 | 0.0 | 0.0 | 0.0 | 97.0 | 95.0 |
| | HYDROCHLORIC ACID | 2 | % V/V | | | | | | |
| 16 | PCC-1133 | .0313 | % V/V | 0.0 | 0.0 | 0.0 | 0.0 | 30.0 | 30.0 |
| | NITRIC ACID | 2 | LB AE/A | | | | | | |
| 17 | PCC-1133 | .0625 | % V/V | 0.0 | 0.0 | 0.0 | 0.0 | 60.0 | 60.0 |
| | NITRIC ACID | 2 | LB AE/A | | | | | | |
| 18 | PCC-1133 | 0.125 | % V/V | 0.0 | 0.0 | 0.0 | 0.0 | 60.0 | 60.0 |
| | NITRIC ACID | 2 | LB AE/A | | | | | | |
| 19 | PCC-1133 | 0.25 | % V/V | 0.0 | 0.0 | 0.0 | 0.0 | 83.3 | 85.0 |
| | NITRIC ACID | 2 | LB AE/A | | | | | | |
| 20 | PCC-1133 | 0.5 | % V/V | 0.0 | 0.0 | 0.0 | 0.0 | 88.3 | 90.0 |
| | NITRIC ACID | 2 | LB AE/A | | | | | | |
| 21 | PCC-1133 | .0313 | % V/V | 0.0 | 0.0 | 0.0 | 0.0 | 40.0 | 20.0 |
| | GLACIAL ACETIC ACID | 2 | LB AE/A | | | | | | |
| 22 | PCC-1133 | .0625 | % V/V | 0.0 | 0.0 | 0.0 | 0.0 | 50.0 | 30.0 |
| | GLACIAL ACETIC ACID | 2 | LB AE/A | | | | | | |
| 23 | PCC-1133 | 0.125 | % V/V | 0.0 | 0.0 | 0.0 | 0.0 | 65.0 | 70.0 |
| | GLACIAL ACETIC ACID | 2 | LB AE/A | | | | | | |
| 24 | PCC-1133 | 0.25 | % V/V | 0.0 | 0.0 | 0.0 | 0.0 | 65.0 | 70.0 |
| | GLACIAL ACETIC ACID | 2 | LB AE/A | | | | | | |
| 25 | PCC-1133 | 0.5 | % V/V | 0.0 | 0.0 | 0.0 | 0.0 | 85.0 | 80.0 |
| | GLACIAL ACETIC ACID | 2 | % V/V | | | | | | |
| 26 | PCC-1133 | 0313 | LB AE/A | 0.0 | 0.0 | 0.0 | 0.0 | 50.0 | 40.0 |
| | PHOSPHORIC ACID | 2 | % V/V | | | | | | |
| 27 | PCC-1133 | .0625 | LB AE/A | 0.0 | 0.0 | 0.0 | 0.0 | 50.0 | 40.0 |
| | PHOSPHORIC ACID | 2 | % V/V | | | | | | |
| 28 | PCC-1133 | 0.125 | LB AE/A | 0.0 | 0.0 | 0.0 | 0.0 | 85.0 | 60.0 |
| | PHOSPHORIC ACID | 2 | % V/V | | | | | | |
| 29 | PCC-1133 | 0.25 | LB AE/A | 0.0 | 0.0 | 0.0 | 0.0 | 90.0 | 80.0 |
| | PHOSPHORIC ACID | 2 | % V/V | | | | | | |
| 30 | PCC-1133 | 0.5 | LB AE/A | 0.0 | 0.0 | 0.0 | 0.0 | 95.0 | 90.0 |
| | PHOSPHORIC ACID | 2 | % V/V | | | | | | |
| 31 | PCC-1133 | .0313 | LB AE/A | 0.0 | 0.0 | 0.0 | 0.0 | 30.0 | 30.0 |
| | PERCHLORIC ACID | 2 | % V/V | | | | | | |
| 32 | PCC-1133 | .0625 | LB AE/A | 0.0 | 0.0 | 0.0 | 0.0 | 40.0 | 30.0 |
| | PERCHLORIC ACID | 2 | % V/V | | | | | | |
| 33 | PCC-1133 | 0.125 | LB AE/A | 0.0 | 0.0 | 0.0 | 0.0 | 50.0 | 60.0 |
| | PERCHLORIC ACID | 2 | % V/V | | | | | | |
| 34 | PCC-1133 | 0.25 | LB AE/A | 0.0 | 0.0 | 0.0 | 0.0 | 75.0 | 60.0 |
| | PERCHLORIC ACID | 2 | % V/V | | | | | | |
| 35 | PCC-1133 | 0.5 | LB AE/A | 0.0 | 0.0 | 0.0 | 0.0 | 85.0 | 70.0 |
| | PERCHLORIC ACID | 2 | % V/V | | | | | | |
| 36 | PCC-1133 | .0313 | LB AE/A | 0.0 | 0.0 | 0.0 | 0.0 | 50.0 | 40.0 |
| | POLYPHOSPHORIC ACID | 2 | % V/V | | | | | | |
| 37 | PCC-1133 | .0625 | LB AE/A | 0.0 | 0.0 | 0.0 | 0.0 | 60.0 | 40.0 |
| | POLYPHOSPHORIC ACID | 2 | % V/V | | | | | | |
| 38 | PCC-1133 | 0.125 | LB AE/A | 0.0 | 0.0 | 0.0 | 0.0 | 60.0 | 60.0 |
| | POLYPHOSPHORIC ACID | 2 | % V/V | | | | | | |
| 39 | PCC-1133 | 0.25 | LB AE/A | 0.0 | 0.0 | 0.0 | 0.0 | 85.0 | 80.0 |
| | POLYPHOSPHORIC ACID | 2 | % V/V | | | | | | |
| 40 | PCC-1133 | 0.5 | LB AE/A | 0.0 | 0.0 | 0.0 | 0.0 | 90.0 | 90.0 |
| | POLYPHOSPHORIC ACID | 2 | % V/V | | | | | | |
| 41 | SABER | .0313 | LB AE/A | 0.0 | 0.0 | 0.0 | 0.0 | 10.0 | 5.0 |
| 42 | SABER | .0625 | LB AE/A | 0.0 | 0.0 | 0.0 | 0.0 | 30.0 | 10.0 |
| 43 | SABER | 0.125 | LB AE/A | 0.0 | 0.0 | 0.0 | 0.0 | 50.0 | 20.0 |
| 44 | SABER | 0.25 | LB AE/A | 0.0 | 0.0 | 0.0 | 0.0 | 60.0 | 60.0 |
| 45 | SABER | 0.5 | LB AE/A | 0.0 | 0.0 | 0.0 | 0.0 | 60.0 | 60.0 |
| 46 | UNTREATED | | | 0.0 | 0.0 | 0.0 | 0.0 | 0.0 | 0.0 |

DATA FOR EXPERIMENT 4 (TWO WEEK)

| | | Rate | Units | Corn | tame oat | *kochia* | wheat | dry bean | sunflower |
|---|---|---|---|---|---|---|---|---|---|
| 1 | PCC-1133 | .0313 | LB AE/A | 0.0 | 0.0 | 0.0 | 0.0 | 0.0 | 5.0 |
| 2 | PCC-1133 | .0625 | LB AE/A | 0.0 | 0.0 | 0.0 | 0.0 | 40.0 | 20.0 |
| 3 | PCC-1133 | 0.125 | LB AE/A | 0.0 | 0.0 | 0.0 | 0.0 | 50.0 | 40.0 |
| 4 | PCC-1133 | 0.25 | LB AE/A | 0.0 | 0.0 | 0.0 | 0.0 | 70.0 | 70.0 |
| 5 | PCC-1133 | 0.5 | LB AE/A | 0.0 | 0.0 | 0.0 | 0.0 | 85.0 | 85.0 |
| 6 | PCC-1133 | .0313 | LB AE/A | 0.0 | 0.0 | 0.0 | 0.0 | 50.0 | 40.0 |
| | SULFURIC ACID | 2 | % V/V | | | | | | |

-continued

| | | Rate | Units | Corn | tame oat | *kochia* | wheat | dry bean | sunflower |
|---|---|---|---|---|---|---|---|---|---|
| 7 | PCC-1133 SULFURIC ACID | .0625 2 | LB AE/A % V/V | 0.0 | 0.0 | 0.0 | 0.0 | 60.0 | 60.0 |
| 8 | PCC-1133 SULFURIC ACID | 0.125 2 | LB AE/A % V/V | 0.0 | 0.0 | 0.0 | 0.0 | 80.0 | 70.0 |
| 9 | PCC-1133 SULFURIC ACID | 0.25 2 | LB AE/A % V/V | 0.0 | 0.0 | 0.0 | 0.0 | 90.0 | 80.0 |
| 10 | PCC-1133 SULFURIC ACID | 0.5 2 | LB AE/A % V/V | 0.0 | 0.0 | 0.0 | 0.0 | 95.0 | 88.3 |
| 11 | PCC-1133 HYDROCHLORIC ACID | .0313 2 | LB AE/A % V/V | 0.0 | 0.0 | 0.0 | 0.0 | 60.0 | 50.0 |
| 12 | PCC-1133 HYDROCHLORIC ACID | .0625 2 | LB AE/A % V/V | 0.0 | 0.0 | 0.0 | 0.0 | 60.0 | 50.0 |
| 13 | PCC-1133 HYDROCHLORIC ACID | 0.125 2 | LB AE/A % V/V | 0.0 | 0.0 | 0.0 | 0.0 | 70.0 | 70.0 |
| 14 | PCC-1133 HYDROCHLORIC ACID | 0.25 2 | LB AE/A % V/V | 0.0 | 0.0 | 0.0 | 0.0 | 90.0 | 85.0 |
| 15 | PCC-1133 HYDROCHLORIC ACID | 0.5 2 | LB AE/A % V/V | 0.0 | 0.0 | 0.0 | 0.0 | 99.0 | 97.0 |
| 16 | PCC-1133 NITRIC ACID | .0313 2 | % V/V LB AE/A | 0.0 | 0.0 | 0.0 | 0.0 | 40.0 | 30.0 |
| 17 | PCC-1133 NITRIC ACID | .0625 2 | % V/V LB AE/A | 0.0 | 0.0 | 0.0 | 0.0 | 60.0 | 60.0 |
| 18 | PCC-1133 NITRIC ACID | 0.125 2 | °A V/V LB AE/A | 0.0 | 0.0 | 0.0 | 0.0 | 60.0 | 60.0 |
| 19 | PCC-1133 NITRIC ACID | 0.25 2 | % V/V LB AE/A | 0.0 | 0.0 | 0.0 | 0.0 | 90.0 | 85.0 |
| 20 | PCC-1133 NITRIC ACID | 0.5 2 | % V/V LB AE/A | 0.0 | 0.0 | 0.0 | 0.0 | 93.0 | 90.0 |
| 21 | PCC-1133 GLACIAL ACETIC ACID | .0313 2 | % V/V LB AE/A | 0.0 | 0.0 | 0.0 | 0.0 | 50.0 | 30.0 |
| 22 | PCC-1133 GLACIAL ACETIC ACID | .0625 2 | % V/V LB AE/A | 0.0 | 0.0 | 0.0 | 0.0 | 50.0 | 30.0 |
| 23 | PCC-1133 GLACIAL ACETIC ACID | 0.125 2 | °A V/V LB AE/A | 0.0 | 0.0 | 0.0 | 0.0 | 65.0 | 65.0 |
| 24 | PCC-1133 GLACIAL ACETIC ACID | 0.25 2 | % V/V LB AE/A | 0.0 | 0.0 | 0.0 | 0.0 | 70.0 | 70.0 |
| 25 | PCC-I 133 GLACIAL ACETIC ACID | 0.5 2 | % V/V % V/V | 0.0 | 0.0 | 0.0 | 0.0 | 95.0 | 90.0 |
| 26 | PCC-1133 PHOSPHORIC ACID | .0313 2 | LB AE/A % V/V | 0.0 | 0.0 | 0.0 | 0.0 | 60.0 | 50.0 |
| 27 | PCC-1133 PHOSPHORIC ACID | .0625 2 | LB AE/A % V/V | 0.0 | 0.0 | 0.0 | 0.0 | 60.0 | 50.0 |
| 28 | PCC-1133 PHOSPHORIC ACID | 0.125 2 | LB AE/A % V/V | 0.0 | 0.0 | 0.0 | 0.0 | 85.0 | 70.0 |
| 29 | PCC-1133 PHOSPHORIC ACID | 0.25 2 | LB AE/A % V/V | 0.0 | 0.0 | 0.0 | 0.0 | 90.0 | 80.0 |
| 30 | PCC-1133 PHOSPHORIC ACID | 0.5 2 | LB AE/A % V/V | 0.0 | 0.0 | 0.0 | 0.0 | 97.0 | 93.0 |
| 31 | PCC-1133 PERCHLORIC ACID | .0313 2 | LB AE/A % V/V | 0.0 | 0.0 | 0.0 | 0.0 | 40.0 | 30.0 |
| 32 | PCC-1133 PERCHLORIC ACID | .0625 2 | LB AE/A % V/V | 0.0 | 0.0 | 0.0 | 0.0 | 50.0 | 30.0 |
| 33 | PCC-1133 PERCHLORIC ACID | 0.125 2 | LB AE/A % V/V | 0.0 | 0.0 | 0.0 | 0.0 | 50.0 | 60.0 |
| 34 | PCC-1133 PERCHLORIC ACID | 0.25 2 | LB AE/A % V/V | 0.0 | 0.0 | 0.0 | 0.0 | 75.0 | 70.0 |
| 35 | PCC-1133 PERCHLORIC ACID | 0.5 2 | LB AE/A % V/V | 0.0 | 0.0 | 0.0 | 0.0 | 85.0 | 80.0 |
| 36 | PCC-1133 POLYPHOSPHORIC ACID | .0313 2 | LB AE/A % V/V | 0.0 | 0.0 | 0.0 | 0.0 | 50.0 | 20.0 |
| 37 | PCC-1133 POLYPHOSPHORIC ACID | .0625 2 | LB AE/A % V/V | 0.0 | 0.0 | 0.0 | 0.0 | 55.0 | 40.0 |
| 38 | PCC-1133 POLYPHOSPHORIC ACID | 0.125 2 | LB AE/A % V/V | 0.0 | 0.0 | 0.0 | 0.0 | 65.0 | 60.0 |
| 39 | PCC-1133 POLYPHOSPHORIC ACID | 0.25 2 | LB AE/A % V/V | 0.0 | 0.0 | 0.0 | 0.0 | 85.0 | 85.0 |

| DATA FOR EXPERIMENT 4 (TWO WEEK) | | | | | | | | |
|---|---|---|---|---|---|---|---|---|
| | | Rate | Units | Corn | tame oat | *kochia* | wheat | dry bean | sunflower |
| 40 | PCC-1133 POLYPHOSPHORIC ACID | 0.5 2 | LB AE/A % V/V | 0.0 | 0.0 | 0.0 | 0.0 | 91.7 | 90.0 |
| 41 | SABER | .0313 | LB AE/A | 0.0 | 0.0 | 0.0 | 0.0 | 10.0 | 5.0 |
| 42 | SABER | .0625 | LB AE/A | 0.0 | 0.0 | 0.0 | 0.0 | 20.0 | 10.0 |
| 43 | SABER | 0.125 | LB AE/A | 0.0 | 0.0 | 0.0 | 0.0 | 50.0 | 50.0 |
| 44 | SABER | 0.25 | LB AE/A | 0.0 | 0.0 | 0.0 | 0.0 | 70.0 | 70.0 |
| 45 | SABER | 0.5 | LB AE/A | 0.0 | 0.0 | 0.0 | 0.0 | 75.0 | 75.0 |
| 46 | UNTREATED | | | 0.0 | 0.0 | 0.0 | 0.0 | 0.0 | 0.0 |

| DATA FOR EXPERIMENT 5 (TWO WEEK) | | | | | | | | |
|---|---|---|---|---|---|---|---|---|
| | | Rate | Unit | corn | tame oat | *kochia* | spring wheat | dry bean | sunflower |
| 1 | PCC-1168 | .0313 | LB AE/A | 0.0 | 0.0 | 0.0 | 0.0 | 5.0 | 0.0 |
| 2 | PCC-1168 | .0625 | LB AE/A | 0.0 | 0.0 | 0.0 | 10.0 | 30.0 | 20.0 |
| 3 | PCC-1168 | 0.125 | LB AE/A | 20.0 | 20.0 | 0.0 | 40.0 | 50.0 | 60.0 |
| 4 | PCC-1168 | 0.25 | LB AE/A | 60.0 | 60.0 | 20.0 | 70.0 | 70.0 | 95.0 |
| 5 | PCC-1168 | 0.5 | LB AE/A | 75.0 | 70.0 | 50.0 | 80.0 | 75.0 | 100.0 |
| 6 | PCC-1168 SULFURIC ACID | .0313 4 | LB AE/A % V/V | 0.0 | 0.0 | 0.0 | 10.0 | 50.0 | 60.0 |
| 7 | PCC-1168 SULFURIC ACID | .0625 4 | LB AE/A % V/V | 10.0 | 30.0 | 0.0 | 30.0 | 70.0 | 90.0 |
| 8 | PCC-1168 SULFURIC ACID | 0.125 4 | LB AE/A % V/V | 65.0 | 60.0 | 10.0 | 65.0 | 80.0 | 95.0 |
| 9 | PCC-1168 SULFURIC ACID | 0.25 4 | LB AE/A % V/V | 80.0 | 75.0 | 50.0 | 85.0 | 85.0 | 100.0 |
| 10 | PCC-1168 SULFURIC ACID | 0.5 4 | LB AE/A % V/V | 100.0 | 100.0 | 95.0 | 100.0 | 98.0 | 100.0 |
| 11 | PCC-1168 HYDROCHLORIC ACID | .0313 4 | LB AE/A % V/V | 0.0 | 0.0 | 0.0 | 0.0 | 30.0 | 20.0 |
| 12 | PCC-1168 HYDROCHLORIC ACID | .0625 4 | LB AE/A % V/V | 0.0 | 0.0 | 0.0 | 10.0 | 50.0 | 65.0 |
| 13 | PCC-1168 HYDROCHLORIC ACID | 0.125 4 | LB AE/A % V/V | 10.0 | 25.0 | 0.0 | 40.0 | 60.0 | 70.0 |
| 14 | FCC-1168 HYDROCHLORIC ACID | 0.25 4 | LB AE/A % V/V | 75.0 | 70.0 | 10.0 | 60.0 | 80.0 | 90.0 |
| 15 | PCC-1168 HYDROCHLORIC ACID | 0.5 4 | LB AE/A % V/V | 80.0 | 90.0 | 60.0 | 90.0 | 93.0 | 100.0 |
| 16 | PCC-1168 NITRIC ACID | 0313 4 | % V/V LB AE/A | 0.0 | 0.0 | 0.0 | 0.0 | 50.0 | 50.0 |
| 17 | PCC-1168 NITRIC ACID | .0625 4 | % V/V LB AE/A | 0.0 | 0.0 | 0.0 | 10.0 | 55.0 | 65.0 |
| 18 | FCC-1168 NITRIC ACID | 0.125 4 | % V/V LB AE/A | 15.7 | 25.0 | 10.0 | 40.0 | 60.0 | 75.0 |
| 19 | PCC-1168 NITRIC ACID | 0.25 4 | % V/V LB AE/A | 75.0 | 70.0 | 60.0 | 60.0 | 80.0 | 90.0 |
| 20 | PCC-1168 NITRIC ACID | 0.5 4 | % V/V LB AE/A | 80.0 | 85.0 | 60.0 | 85.0 | 90.0 | 98.0 |
| 21 | PCC-1168 GLACIAL ACETIC ACID | .0313 4 | % V/V LB AE/A | 0.0 | 0.0 | 0.0 | 0.0 | 0.0 | 0.0 |
| 22 | P...,C-1168 GLACIAL ACETIC ACID | .0625 4 | % V/V LB AE/A | 0.0 | 0.0 | 0.0 | 0.0 | 0.0 | 5.0 |
| 23 | PCC-1168 GLACIAL ACETIC ACID | 0.125 4 | % V/V LB AE/A | 10.0 | 20.0 | 0.0 | 36.7 | 30.0 | 40.0 |
| 24 | PCC-1168 GLACIAL ACETIC ACID | 0.25 4 | % V/V LB AE/A | 60.0 | 60.0 | 0.0 | 70.0 | 50.0 | 60.0 |
| 25 | PCC-1168 GLACIAL ACETIC ACID | 0.5 4 | % V/V % V/V | 75.0 | 75.0 | 20.0 | 80.0 | 70.0 | 95.0 |
| 26 | PCC-1168 PHOSPHORIC ACID | .0313 4 | LB AE/A % V/V | 5.0 | 0.0 | 0.0 | 0.0 | 30.0 | 40.0 |
| 27 | PCC-1168 PHOSPHORIC ACID | .0625 4 | LB AE/A % V/V | 15.0 | 0A | 5.0 | 0.0 | 40.0 | 65.0 |
| 28 | PCC-1168 PHOSPHORIC ACID | 0.125 4 | LB AE/A % V/V | 60.7 | 60.0 | 10.0 | 65.0 | 50.0 | 60.0 |

-continued

DATA FOR EXPERIMENT 5 (TWO WEEK)

| | | Rate | Unit | corn | tame oat | *kochia* | spring wheat | dry bean | sunflower |
|---|---|---|---|---|---|---|---|---|---|
| 29 | PCC-1168 PHOSPHORIC ACID | 0.25 4 | LB AE/A % V/V | 80.0 | 75.0 | 20.0 | 85.0 | 70.0 | 95.0 |
| 30 | PCC-1168 PHOSPHORIC ACID | 0.5 4 | LB AE/A % V/V | 93.0 | 95.0 | 80.0 | 95.0 | 98.0 | 100.0 |
| 31 | PCC-1168 PERCHLORIC ACID | .0313 4 | LB AE/A % V/V | 0.0 | 0.0 | 0.0 | 0.0 | 40.0 | 40.0 |
| 32 | PCC-1168 PERCHLORIC ACID | .0625 4 | LB AE/A % V/V | 20.0 | 20.0 | 0.0 | 20.0 | 50.0 | 60.0 |
| 33 | PCC-1168 PERCHLORIC ACID | 0.125 4 | LB AE/A % V/V | 65.0 | 60.0 | 20.0 | 60.0 | 55.0 | 60.0 |
| 34 | PCC-1168 PERCHLORIC ACID | 0.25 4 | LB AE/A % V/V | 80.0 | 75.0 | 30.0 | 75.0 | 60.0 | 95.0 |
| 35 | PCC-1168 PERCHLORIC ACID | 0.5 4 | LB AE/A % V/V | 90.0 | 90.0 | 30.0 | 90.0 | 80.0 | 98.0 |
| 36 | PCC-1168 POLYPHOSPHORIC ACID | .0313 4 | LB AE/A % V/V | 70.0 | 70.0 | 0.0 | 60.0 | 50.0 | 50.0 |
| 37 | PCC-1168 POLYPHOSPHORIC ACID | .0625 4 | LB AE/A % V/V | 75.0 | 75.0 | 0.0 | 75.0 | 55.0 | 65.0 |
| 38 | PCC-1168 POLYPHOSPHORIC ACID | 0.125 4 | LB AE/A % V/V | 80.0 | 80.0 | 30.0 | 90.0 | 60.0 | 90.0 |
| 39 | PCC-1168 POLYPHOSPHORIC ACID | 0.25 4 | LB AE/A % V/V | 95.0 | 90.0 | 40.0 | 93.0 | 85.0 | 95.0 |
| 40 | PCC-1168 POLYPHOSPHORIC ACID | 0.5 4 | LB AE/A % V/V | 98.0 | 95.0 | 80.0 | 95.0 | 90.0 | 100.0 |
| 41 | UNTREATED | | | 0.0 | 10.0 | 0.0 | 0.0 | 0.0 | 0.0 |

Examples 6-8

Examples of certain exemplary suspension concentrate herbicide compositions according to the invention can contain 4 lb. imidazolinone acid per gallon and can be prepared from ingredients including those described in Examples 6-8. In examples 6-8 "AI" means "active ingredient."

Example 6

Example 6 is an exemplary suspension concentrate that includes a 4 lb. per gallon imidazolinone acid (imazethapyr acid), anionic surfactant, anionic dispersant, thickener, and anti-microbial agent.

TABLE 6

Example 6 Ingredients

| Ingredient | % AI-Tech | % Weight | % AI |
|---|---|---|---|
| Water | | 44.90 | |
| SAG 30 Antifoam, Witco | | 0.3 | |
| Diethylene Glycol, freeze depressant, Dow | | 5.00 | |
| Morwet EFW Wetter, Witco | | 1.00 | |
| Imazethapyr Acid | 98.0 | 40.80 | 39.98 |
| Morwet D425, dispersant, Witco | | 3.00 | |
| 2% Kelzan —0.5% Proxel Premix, thickener, Antimicrobial | | 5.00 | |
| Total | | 100 | |

Morwet EFW is a mixture of alkyl napthonate sulfonates.

Example 7

Example 7 is an exemplary suspension concentrate that includes a 4 lb. per gallon imidazolinone acid (imazethapyr acid), acidifying agent, anionic surfactant, anionic dispersant, and thickener.

TABLE 7

Example 7 Ingredients

| Ingredient | % AI-Tech | % Weight | % AI |
|---|---|---|---|
| Water | | 44.70 | |
| SAG 30 Antifoam, Witco | | 0.3 | |
| Diethylene Glycol, freeze depressant, Dow | | 4.00 | |
| Unite, Loveland Industries, surfactant & acidifier, anionic | | 1.00 | |
| Imazethapyr Acid | 98.0 | 42.00 | 41.16 |
| Soprophor FLK, Rhodia, Anionic dispersant | | 2.50 | |
| 72% Phosphoric Acid, acidifier | | 0.50 | |
| Attaflow FL, Englehard, clay thickener | | 5.00 | |
| Total | — | 100 | — |

Example 8

Example 8 is an exemplary suspension concentrate that includes a 4 lb. per gallon imidazolinone acid (imazethapyr acid), nonionic surfactant, nonionic dispersant, thickener, and anti-microbial agent.

TABLE

Example 8 Ingredients

| Ingredient | % AI-Tech | % Weight | % AI |
|---|---|---|---|
| Water | | 54.20 | |
| SAG 30 Antifoam, Witco | | 0.3 | |
| Propylene Glycol, freeze depressant, Dow | | 5.00 | |
| Surfonic L12-6, wetting agent, nonionic, Huntsman | | 1.00 | |
| Imazethapyr Acid | 98.0 | 31.00 | 30.38 |
| Tersperse 4894, dispersant, nonionic, Huntsman | | 3.00 | |
| 2% Kelzan —0.5% Proxel Premix, thickener, Antimicrobial | | 5.00 | |
| Total | — | 100 | — |

Examples 9-10

The following examples illustrate how exemplary suspension concentrates of the invention containing exemplary imidazolinone acid active herbicide compounds, can be used to control plant growth. PCC-1190 and PCC-1189 are examples of suspension concentrates having 3 pounds of imidazolinone acid active herbicide compound per gallon.

Materials and Methods:

Examples 9-10 represent experiments conducted to evaluate the efficacy of a variety of different types of herbicide formulations, including formulations from suspension concentrates, and to evaluate the effect of adding acids to the spray solution as an acidifying agent. Each treatment in the experiment was replicated three times. An untreated control was also included in the experiment.

Examples 9-10 were designed to determine the effect of adding four different acidifying agents (i.e., PCC-1174, LI-136, sulfuric acid, and phosphoric acid) to formulations of imidazolinone acid (PCC-1190 and PCC-1189) and the effect of applying each formulation at six different rates (see data tables). These treatments were compared to PCC-1190 and PCC-1189 without the addition of an acidifying agent, a standard imidazolinone acid formulation (PURSUIT and SCEPTER), and an untreated control.

PCC-1189 Suspension Concentrate Formulation
PCC-1189 contains the active ingredient imazaquin acid.

| INGREDIENT | % AI-Tech | %/WT |
|---|---|---|
| Water | | 54.20 |
| SAG 30, OSI, Antifoam | | 0.30 |
| Proplyene Glycol, Antifreeze | | 5.00 |
| Surfonic L12-6, Huntsman, nonionic wetting agent | | 1.00 |
| Imazaquin Acid, Nat China, Active Ingredient | 95.00 | 31.00 |
| Tersperse 4894, Huntsman, nonionic dispersant/wetter | | 3.50 |
| Attaflow FL | | 5.00 |
| | | 100.00 |

Add in order listed to cowles high speed mixer stopping prior to Attaflow FL thickener addition. Grind to 5-18 microns, 4 hrs in attritor, 60%.

Let down to mix tank with scales

Add calculated amount of thickener (accounting for amount of batch that stays in the attritor) to milled liquid. Blend moderately for 30 min.

PCC-1190 Suspension Concentrate Formulation
PCC-1190 contains the active ingredient imazethapyr acid.

| INGREDIENT | % AI-Tech | %/WT |
|---|---|---|
| Water | | 54.20 |
| SAG 30, OSI, Antifoam | | 0.30 |
| Proplyene Glycol, Antifreeze | | 5.00 |
| Surfonic L12-6, Huntsman, nonionic wetting agent | | 1.00 |
| Imazethapyr Acid, Nat China, Active Ingredient | 98.00 | 31.00 |
| Tersperse 4894, Huntsman, nonionic dispersant/wetter | | 3.50 |
| Attaflow FL | 5.00 | |
| | | 100.00 |

Add in order listed to cowles high speed mixer stopping prior to Attaflow FL thickener addition. Grind to 5-18 microns, 4 hrs in attritor, 60%.

Let down to mix tank with scales

Add calculated amount of thickener (accounting for amount of batch that stays in the attritor) to milled liquid. Blend moderately for 30 min.

PURSUIT® is a commercially available product containing the active ingredient imazethapyr acid. PURSUIT® is formulated as a 2SL ("2SL" means a "two pound per gallon soluble liquid"). SCEPTER® is a commercially available product containing the active ingredient imazaquin acid.

Acidifying Agents

Sulfuric Acid—0.9%

Phosphoric Acid—0.9%

PCC-1174 Acidifying Agent, see supra.

LI-136 acidifying agent, see supra

Procedure

For the experiments, greenhouse flats 26 cm by 6 cm deep were filled with Metro Mix 350 potting soil. The soil was pre-wetted before filling the flats. Six furrows were pressed into the soil in each flat using a custom designed form. Corn, tame oats, velvet leaf (not used in Example 10), wheat, pinto beans, and sunflower were planted in each tray. One species was planted in each of the six rows in each flat. Five seeds were planted in each row of corn, pinto bean, and sunflower. Six seeds were planted in each row of tame oat and wheat. Because velvet leaf seeds were so small, the seeds were sprinkled in each row and the number of such seeds were not counted. Each flat was covered with 2 cm of Metro Mix 350 potting soil and placed in the greenhouse. Greenhouse conditions were 28/20 C day/night temperatures and 16/8 h day/night periods. Light was supplemented with 400 W sodium halide lights. The plants were allowed to germinate and grow in the greenhouse for 2 weeks and then treated. Treatments were mixed using serial dilutions. Each dilution reduced the herbicide rate by one half. All acidifying agents (e.g., PCC-I174, LI-136, sulfuric acid, and phosphoric acid) were calculated and mixed to provide acid concentrations of 0.9%.

After mixing, the pH of the spray solution of each treatment was measured with a VWR Scientific model 8005 pH meter. The pH was measured to determine if the acid used or the amount of acid added was sufficient to lower the pH below the pKa of the acid herbicides used.

At the time of treatment, crops were at the following stages: corn—2 to 3 lf, tame oat—2 to 3 lf, velvet leaf 2 if (not used in Example 10), pinto bean—2-3 lf, wheat—4 to 5 lf, and sunflower-2 lf. Plants were treated using a greenhouse track sprayer equipped with an 8001E nozzle and calibrated to deliver 140 L ha-1 at the height of the crop canopy. Each treatment was simultaneously applied to three trays of plants, one for each replicate. After treatment, the plants were left in the head house to dry and then transferred to the greenhouse. Plants in each treatment were evaluated visually for injury 1 week and 2 weeks after treatment.

Summary of Variables of Example 9

| Acid Treatments | Volumes of each Acid (v/v %) | Herbicide | Herbicide Rate (lb AE/A) | Plants | Reps |
|---|---|---|---|---|---|
| PCC-1174 | 2 | PCC-1190 | 1 | Corn, | 3 |
| Sulfuric | | | 0.5 | Tame oat, | |
| Phosphoric | | | 0.25 | Velvet leaf, wheat | |
| LI-136 | | | 0.125 | | |
| | | | 0.063 | Pinto bean, | |
| | | | 0.0313 | Sunflower | |

Following are data that illustrate the efficacy of various herbicide compositions of Examples 9-10 and Summary of Variables of Example 10. The injury caused by the herbicide treatment was rated visually. Plants were observed and compared to the untreated control. All the plants of each species in each replication were given a single rating. A rating of 0=no injury—the plants look the same as the untreated. A rating of 100=dead—usually highly necrotic, brown and no chance of producing seed.

Each of the acids was combined with the PCC-1190 or PCC-1189 herbicide compositions to form a solution that contains 2 percent by volume of a given 0.9% (of the acid) concentrated acidifying agent (e.g., PCC-1174, LI-136, sulfuric acid, and phosphoric acid), as indicated, and such that the pH of the herbicide composition was below the pKa of the particular herbicide compound.

The ingredients of the herbicide compositions as applied are listed in the following tables, and were diluted with water and used at the rates indicated for herbicide ingredients and acidifying agents.

| | Herbicide | Rate | Units | Corn | Tame Oat | Velvet Leaf | Wheat | Pinto Bean | Sunflower |
|---|---|---|---|---|---|---|---|---|---|
| 1 | PURSUIT | .0313 | LB AE/A | 0.0 | 10.0 | 50.0 | 10.0 | 10.0 | 50.0 |
| 2 | PURSUIT | 0.063 | LB AE/A | 0.0 | 20.0 | 50.0 | 20.0 | 10.0 | 50.0 |
| 3 | PURSUIT | 0.125 | LB AE/A | 0.0 | 30.0 | 50.0 | 20.0 | 20.0 | 50.0 |
| 4 | PURSUIT | 0.25 | LB AE/A | 0.0 | 50.0 | 50.0 | 20.0 | 30.0 | 70.0 |
| 5 | PURSUIT | 0.5 | LB AE/A | 0.0 | 60.0 | 50.0 | 30.0 | 40.0 | 90.0 |
| 6 | PURSUIT | 1 | LB AE/A | 10.0 | 60.0 | 50.0 | 50.0 | 40.0 | 98.0 |
| 7 | PCC-1190 | .0313 | LB AE/A | 0.0 | 10.0 | 50.0 | 10.0 | 10.0 | 50.0 |
| 8 | PCC-1190 | 0.063 | LB AE/A | 0.0 | 20.0 | 50.0 | 20.0 | 20.0 | 50.0 |
| 9 | PCC-1190 | 0.125 | LB AE/A | 0.0 | 30.0 | 50.0 | 20.0 | 20.0 | 60.0 |
| 10 | PCC-1190 | 0.25 | LB AE/A | 0.0 | 50.0 | 50.0 | 30.0 | 40.0 | 70.0 |
| 11 | PCC-1190 | 0.5 | LB AE/A | 0.0 | 60.0 | 50.0 | 40.0 | 40.0 | 90.0 |
| 12 | PCC-1190 | 1 | LB AE/A | 0.0 | 60.0 | 50.0 | 50.0 | 60.0 | 98.0 |
| 13 | PCC-1190 PCC-1174 | .0313 2 | LB AE/A % V/V | 0.0 | 20.0 | 50.0 | 10.0 | 10.0 | 50.0 |
| 14 | PCC-1190 PCC-1174 | 0.063 2 | LB AE/A % V/V | 0.0 | 20.0 | 50.0 | 10.0 | 10.0 | 50.0 |
| 15 | PCC-1190 PCC-1174 | .0125 2 | LB AE/A % V/V | 0.0 | 30.0 | 50.0 | 20.0 | 20.0 | 70.0 |
| 16 | PCC-1190 PCC-1174 | 0.25 2 | LB AE/A % V/V | 0.0 | 50.0 | 50.0 | 20.0 | 30.0 | 80.0 |
| 17 | PCC-1190 PCC-1174 | 0.5 2 | LB AE/A % V/V | 0.0 | 60.0 | 50.0 | 30.0 | 40.0 | 98.0 |
| 18 | PCC-1190 PCC-1174 | 1 2 | LB AE/A % VN | 0.0 | 60.0 | 50.0 | 50.0 | 50.0 | 98.0 |
| 19 | PCC-1190 SULFURIC ACID | .0313 2 | LB AE/A % V/V | 0.0 | 10.0 | 50.0 | 10.0 | 10.0 | 40.0 |
| 20 | PCC-1190 SULFURIC ACID | 0.063 2 | LB AE/A % V/V | 0.0 | 20.0 | 50.0 | 20.0 | 20.0 | 50.0 |
| 21 | PCC-1190 SULFURIC ACID | .0125 2 | LB AE/A % V/V | 0.0 | 30.0 | 50.0 | 20.0 | 30.0 | 50.0 |
| 22 | PCC-1190 SULFURIC ACID | 0.25 2 | LB AE/A % V/V | 0.0 | 40.0 | 50.0 | 30.0 | 50.0 | 80.0 |
| 23 | PCC-1190 SULFURIC ACID | 0.5 2 | LB AE/A % V/V | 0.0 | 50.0 | 60.0 | 50.0 | 50.0 | 90.0 |
| 24 | PCC-1190 SULFURIC ACID | 1 2 | LB AE/A % V/V | 0.0 | 60.0 | 60.0 | 50.01 | 60.0 | 98.0 |
| 25 | PCC-1190 PHOSPHORIC ACID | .0313 2 | LB AE/A % V/V | 0.0 | 10.0 | 50.01 | 10.0 | 10.0 | 50.0 |
| 26 | PCC-1190 PHOSPHORIC ACID | 0.063 2 | LB AE/A % V/V | 0.0 | 20.0 | 50.0 | 10.0 | 10.0 | 50.0 |
| 27 | PCC-1190 PHOSPHORIC ACID | .0125 2 | LB AE/A % V/V | 0.0 | 20.01 | 50.0 | 10.0 | 20.0 | 50.0 |
| 28 | PCC-1190 PHOSPHORIC ACID | 0.25 2 | LB AE/A % V/V | 0.0 | 30.0 | 50.0 | 30.0 | 30.01 | 50.0 |
| 29 | PCC-1190 PHOSPHORIC ACID | 0.5 2 | LB AE/A % V/V | 0.0 | 40.0 | 50.0 | 40.0 | 40.0 | 70.0 |

Data for Example 9 (One Week)

| Data for Example 9 (One Week) | | | | | | | | |
|---|---|---|---|---|---|---|---|---|
| | Herbicide | Rate | Units | Corn | Tame Oat | Velvet Leaf | Wheat | Pinto Bean | Sunflower |
| 30 | PCC-1190 | 1 | LB AE/A | 0.0 | 40.0 | 50.0 | 50.0 | 50.0 | 90.0 |
| | PHOSPHORIC ACID | 2 | % V/V | | | | | | |
| 31 | PCC-1190 | .0313 | LB AE/A | 0.0 | 10.0 | 50.0 | 10.0 | 10.0 | 50.0 |
| | LI 136 | 2 | % V/V | | | | | | |
| 32 | PCC-1190 | 0.063 | LB AE/A | 0.0 | 10.0 | 50.0 | 10.0 | 10.0 | 50.0 |
| | LI 136 | 2 | % V/V | | | | | | |
| 33 | PCC-1190 | .0125 | LB AE/A | 0.0 | 20.0 | 50.0 | 20.0 | 20.0 | 50.0 |
| | LI 136 | 2 | % V/V | | | | | | |
| 34 | PCC-1190 | 0.25 | LB AE/A | 0.0 | 40.0 | 50.0 | 20.0 | 30.0 | 70.0 |
| | LI 136 | 2 | % V/V | | | | | | |
| 35 | PCC-1190 | 0.5 | LB AE/A | 0.0 | 40.0 | 50.0 | 30.0 | 30.0 | 70.0 |
| | LI 136 | 2 | % V/V | | | | | | |
| 36 | PCC-1190 | 1 | LB AE/A | 0.0 | 50.0 | 50.0 | 40.0 | 40.0 | 95.0 |
| | LI 136 | 2 | % V/V | | | | | | |
| 37 | UNTREATED | | | 0.0 | 0.0 | 0.0 | 0.0 | 0.0 | 0.0 |

| Data for Example 9 (Two Week) | | | | | | | | |
|---|---|---|---|---|---|---|---|---|
| | Herbicide | Rate | Units | Corn | Tame Oat | Velvet Leaf | Wheat | Pinto Bean | Sunflower |
| 1 | PURSUIT | .0313 | LB AE/A | 20.0 | 20.0 | 50.0 | 20.0 | 30.0 | 50.0 |
| 2 | PURSUIT | 0.063 | LB AE/A | 20.0 | 20.0 | 50.0 | 20.0 | 30.0 | 50.0 |
| 3 | PURSUIT | 0.125 | LB AE/A | 20.0 | 40.0 | 50.0 | 30.0 | 35.0 | 50.0 |
| 4 | PURSUIT | 0.25 | LB AE/A | 20.0 | 50.0 | 60.0 | 40.0 | 35.0 | 70.0 |
| | PURSUIT | 0.5 | LB AE/A | 20.0 | 70.0 | 60.0 | 70.0 | 45.0 | 95.0 |
| 6 | PURSUIT | 1 | LB AE/A | 20.0 | 80.0 | 70.0 | 75.0 | 55.0 | 100.0 |
| 7 | PCC-1190 | .0313 | LB AE/A | 10.0 | 20.0 | 50.0 | 20.0 | 25.0 | 50.0 |
| 8 | PCC-1190 | 0.063 | LB AE/A | 20.0 | 30.0 | 50.0 | 30.0 | 35.0 | 70.0 |
| 9 | PCC-1190 | 0.125 | LB AE/A | 30.0 | 60.0 | 50.0 | 30.0 | 35.0 | 70.0 |
| 10 | PCC-1190 | 0.25 | LB AE/A | 20.0 | 70.0 | 60.0 | 50.0 | 40.0 | 90.0 |
| 11 | PCC-1190 | 0.5 | LB AE/A | 20.0 | 70.0 | 60.0 | 70.0 | 50.0 | 95.0 |
| 12 | PCC-1190 | 1 | LB AE/A | 20.0 | 85.0 | 70.0 | 75.0 | 65.0 | 100.0 |
| 13 | PCC-1190 | .0313 | LB AE/A | 10.0 | 50.0 | 50.0 | 25.0 | 30.0 | 70.0 |
| | PCC-1174 | 2 | % V/V | | | | | | |
| 14 | PCC-1190 | 0.063 | LB AE/A | 10.0 | 50.0 | 50.0 | 40.0 | 30.0 | 80.0 |
| | PCC-1174 | 2 | % V/V | | | | | | |
| 15 | PCC-1190 | .0125 | LB AE/A | 10.0 | 60.0 | 50.0 | 40.0 | 30.0 | 85.0 |
| | PCC-1174 | 2 | % V/V | | | | | | |
| 16 | PCC-1190 | 0.25 | LB AE/A | 10.0 | 70.0 | 60.0 | 50.0 | 50.0 | 95.0 |
| | PCC-1174 | 2 | % V/V | | | | | | |
| 17 | PCC-1190 | 0.5 | LB AE/A | 20.0 | 80.0 | 60.0 | 75.0 | 50.0 | 95.0 |
| | PCC-1174 | 2 | % V/V | | | | | | |
| 18 | PCC-1190 | 1 | LB AE/A | 20.0 | 90.0 | 70.0 | 85.0 | 70.0 | 100.0 |
| | PCC-1174 | 2 | % V/V | | | | | | |

-continued

| | Herbicide | Rate | Units | Corn | Tame Oat | Velvet Leaf | Wheat | Pinto Bean | Sunflower |
|---|---|---|---|---|---|---|---|---|---|
| 19 | PCC-1190 | .0313 | LB AE/A | 20.0 | 50.0 | 50.0 | 25.0 | 30.0 | 70.0 |
| | SULFURIC ACID | 2 | % V/V | | | | | | |
| 20 | PCC-1190 | 0.063 | LB AE/A | 30.0 | 50.0 | 50.0 | 40.0 | 40.0 | 80.0 |
| | SULFURIC ACID | 2 | % V/V | | | | | | |
| 21 | PCC-1190 | .0125 | LB AE/A | 23.3 | 60.0 | 50.0 | 40.0 | 35.0 | 85.0 |
| | SULFURIC ACID | 2 | % V/V | | | | | | |
| 22 | PCC-1190 | 0.25 | LB AE/A | 20.0 | 70.0 | 60.0 | 50.0 | 50.0 | 95.0 |
| | SULFURIC ACID | 2 | % V/V | | | | | | |
| 23 | PCC-1190 | 0.5 | LB AE/A | 10.0 | 80.0 | 65.0 | 75.0 | 65.0 | 95.0 |
| | SULFURIC ACID | 2 | % V/V | | | | | | |
| 24 | PCC-1190 | 1 | LB AE/A | 20.0 | 95.0 | 70.0 | 85.0 | 80.0 | 100.0 |
| | SULFURIC ACID | 2 | % V/V | | | | | | |
| 25 | PCC-1190 | .0313 | LB AE/A | 10.0 | 50.0 | 50.0 | 25.0 | 30.0 | 70.0 |
| | PHOSPHORIC ACID | 2 | % V/V | | | | | | |
| 26 | PCC-1190 | 0.063 | LB AE/A | 20.0 | 50.0 | 50.0 | 40.0 | 30.0 | 80.0 |
| | PHOSPHORIC ACID | 2 | % V/V | | | | | | |
| 27 | PCC-1190 | .0125 | LB AE/A | 10.0 | 56.7 | 50.0 | 35.0 | 30.0 | 85.0 |
| | PHOSPHORIC ACID | 2 | % V/V | | | | | | |
| 28 | PCC-1190 | 0.25 | LB AE/A | 20.0 | 66.7 | 60.0 | 50.0 | 40.0 | 95.0 |
| | PHOSPHORIC ACID | 2 | % V/V | | | | | | |
| 29 | PCC-1190 | 0.5 | LB AE/A | 20.0 | 70.0 | 60.0 | 75.0 | 50.0 | 95.0 |
| | PHOSPHORIC ACID | 2 | % V/V | | | | | | |
| 30 | PCC-1190 | 1 | LB AE/A | 20.0 | 76.7 | 70.0 | 75.0 | 70.0 | 100.0 |
| | PHOSPHORIC ACID | 2 | % V/V | | | | | | |
| 31 | PCC-1190 | .0313 | LB AE/A | 10.0 | 46.7 | 50.0 | 20.0 | 25.0 | 60.0 |
| | LI 136 | 2 | % V/V | | | | | | |
| 32 | PCC-1190 | 0.063 | LB AE/A | 0.0 | 30.0 | 50.0 | 30.0 | 25.0 | 80.0 |
| | LI 136 | 2 | % V/V | | | | | | |
| 33 | PCC-1190 | .0125 | LB AE/A | 10.0 | 30.0 | 50.0 | 30.0 | 30.0 | 70.0 |
| | LI 136 | 2 | % V/V | | | | | | |
| 34 | PCC-1190 | 0.25 | LB AE/A | 15.0 | 50.0 | 60.0 | 35.0 | 30.0 | 85.0 |
| | LI 136 | 2 | % V/V | | | | | | |
| 35 | PCC-1190 | 0.5 | LB AE/A | 20.0 | 63.3 | 60.0 | 50.0 | 45.0 | 90.0 |
| | LI 136 | 2 | % V/V | | | | | | |
| 36 | PCC-1190 | 1 | LB AE/A | 20.0 | 80.0 | 70.0 | 60.0 | 55.0 | 96.7 |
| | LI 136 | 2 | % V/V | | | | | | |
| 37 | UNTREATED | | | 0.0 | 0.0 | 0.0 | 0.0 | 0.0 | 0.0 |

Summary of Variables of Example 10

| Acid Treatments | Volumes of each Acid (v/v %) | Herbicide | Herbicide Rate (lb AE/A) | Plants | Reps |
|---|---|---|---|---|---|
| PCC-1174 SULFURIC PHOSPHORIC | 2 | PCC-1189 | 0.0155 0.031 0.0613 0.1225 0.245 0.49 | Corn, Tame oat, Wheat, Pinto bean, Sunflower | 3 |
| LI-136 | | | | | |

| | Data for Example 10 (Two Week) | | | | | | |
|---|---|---|---|---|---|---|---|
| | Herbicide | Rate | Unit | Corn | Tame Oat | Wheat | Pinto Bean | Sunflower |
| 1 | SCEPTOR | .0155 | LB AE/A | 0.0 | 0.0 | 0.0 | 0.0 | 0.0 |
| 2 | SCEPTOR | 0.031 | LB AE/A | 0.0 | 0.0 | 10.0 | 20.0 | 30.0 |
| 3 | SCEPTOR | .0613 | LB AE/A | 0.0 | 0.0 | 0.0 | 10.0 | 10.0 |
| 4 | SCEPTOR | .1225 | LB AE/A | 10.0 | 0.0 | 0.0 | 10.0 | 30.0 |
| 5 | SCEPTOR | 0.245 | LB AE/A | 10.0 | 0.0 | 0.0 | 20.0 | 60.0 |
| 6 | SCEPTOR | 0.49 | LB AE/A | 20.0 | 10.0 | 10.0 | 20.0 | 60.0 |
| 7 | PCC-1189 | .0155 | LB AE/A | 30.0 | 10.0 | 10.0 | 0.0 | 0.0 |
| 8 | PCC-1189 | 0.031 | LB AE/A | 0.0 | 0.0 | 0.0 | 10.0 | 10.0 |
| 9 | PCC-1189 | .0613 | LB AE/A | 20.0 | 10.0 | 0.0 | 10.0 | 10.0 |
| 10 | PCC-1189 | .1225 | LB AE/A | 20.0 | 10.0 | 10.0 | 10.0 | 60.0 |
| 11 | PCC-1189 | 0.245 | LB AE/A | 40.0 | 20.0 | 10.0 | 20.0 | 60.0 |
| 12 | PCC-1189 | 0.49 | LB AE/A | 30.0 | 10.0 | 10.0 | 10.0 | 70.0 |
| 13 | PCC-1189 | .0155 | LB AE/A | 30.0 | 20.0 | 10.0 | 10.0 | 20.0 |
| 13 | PCC-1174 | 2 | % V/V | 30.0 | 20.0 | 10.0 | 10.0 | 20.0 |
| 14 | PCC-1189 | 0.031 | LB AE/A | 10.0 | 20.0 | 10.0 | 20.0 | 70.0 |
| 14 | PCC-1174 | 2 | % V/V | 10.0 | 20.0 | 10.0 | 20.0 | 70.0 |
| 15 | PCC-I189 | .0613 | LB AE/A | 30.0 | 30.0 | 20.0 | 30.0 | 60.0 |
| 15 | PCC-1174 | 2 | % V/V | 30.0 | 30.0 | 20.0 | 30.0 | 60.0 |
| 16 | PCC-1189 | .1225 | LB AE/A | 40.0 | 30.0 | 20.0 | 30.0 | 70.0 |
| 16 | PCC-I 174 | 2 | % V/V | 40.0 | 30.0 | 20.0 | 30.0 | 70.0 |
| 17 | PCC-1189 | 0.245 | LB AE/A | 50.0 | 30.0 | 20.0 | 40.0 | 60.0 |
| 17 | PCC-1174 | 2 | % V/V | 50.0 | 30.0 | 20.0 | 40.0 | 60.0 |
| 18 | PCC-1189 | 0.49 | LB AE/A | 50.0 | 10.0 | 10.0 | 60.0 | 90.0 |
| 18 | PCC-1174 | 2 | % V/V | 50.0 | 10.0 | 10.0 | 60.0 | 90.0 |
| 19 | PCC-1189 | .0155 | LB AE/A | 10.0 | 0.0 | 0.0 | 10.0 | 30.0 |
| 19 | SULFURIC ACID | 2 | % V/V | 10.0 | 0.0 | 0.0 | 10.0 | 30.0 |
| 20 | PCC-1189 | 0.031 | LB AE/A | 20.0 | 0.0 | 0.0 | 10.0 | 30.0 |
| 20 | SULFURIC ACID | 2 | % V/V | 20.0 | 0.0 | 0.0 | 10.0 | 30.0 |
| 21 | PCC-1189 | .0613 | LB AE/A | 10.0 | 0.0 | 0.0 | 0.0 | 40.0 |
| 21 | SULFURIC ACID | 2 | % V/V | 10.0 | 0.0 | 0.0 | 0.0 | 40.0 |
| 22 | PCC-1189 | .1225 | LB AE/A | 10.0 | 0.0 | 0.0 | 10.0 | 40.0 |
| 22 | SULFURIC ACID | 2 | % V/V | 10.0 | 0.0 | 0.0 | 10.0 | 40.0 |
| 23 | PCC-1189 | 0.245 | LB AE/A | 20.0 | 0.0 | 0.0 | 20.0 | 60.0 |
| 23 | SULFURIC ACID | 2 | % V/V | 20.0 | 0.0 | 0.0 | 20.0 | 60.0 |
| 24 | PCC-1189 | 0.49 | LB AE/A | 20.0 | 10.0 | 10.0 | 30.0 | 80.0 |
| 24 | SULFURIC ACID | 2 | % V/V | 20.0 | 10.0 | 10.0 | 30.0 | 80.0 |
| 25 | PCC-1189 | .0155 | LB AE/A | 10.0 | 0.0 | 0.0 | 10.0 | 50.0 |
| 25 | PHOSPHORIC ACID | 2 | % V/V | 10.0 | 0.0 | 0.0 | 10.0 | 50.0 |
| 26 | PCC-1189 | 0.031 | LB AE/A | 10.0 | 0.0 | 0.0 | 20.0 | 50.0 |
| 26 | PHOSPHORIC ACID | 2 | % V/V | 10.0 | 0.0 | 0.0 | 20.0 | 50.0 |
| 27 | PCC-1189 | .0613 | LB AE/A | 15.0 | 0.0 | 0.0 | 30.0 | 40.0 |
| 27 | PHOSPHORIC ACID | 2 | % V/V | 15.0 | 0.0 | 0.0 | 30.0 | 40.0 |
| 28 | PCC-1189 | .1225 | LB AE/A | 10.0 | 0.0 | 0.0 | 25.0 | 50.0 |
| 28 | PHOSPHORIC ACID | 2 | % V/V | 10.0 | 0.0 | 0.0 | 25.0 | 50.0 |
| 29 | PCC-1189 | 0.245 | 3 AE/A | 10.0 | 0.0 | 0.0 | 30.0 | 60.0 |
| 29 | PHOSPHORIC ACID | 2 | V/V | 10.0 | 0.0 | 0.0 | 30.0 | 60.0 |
| 30 | PCC-1189 | 0.49 | 3 AE/A | 20.0 | 0.0 | 0.0 | 30.0 | 50.0 |
| 30 | PHOSPHORIC ACID | 2 | V/V | 20.0 | 0.0 | 0.0 | 30.0 | 50.0 |
| 31 | PCC-1189 | .0155 | 3 AE/A | 20.0 | 0.0 | 0.0 | 10.0 | 20.0 |
| 31 | LI136 | 2 | V/V | 20.0 | 0.0 | 0.0 | 10.0 | 20.0 |
| 32 | PCC-1189 | 0.031 | 3 AE/A | 20.0 | 0.0 | 0.0 | 10.0 | 10.0 |
| 32 | LI136 | 2 | V/V | 20.0 | 0.0 | 0.0 | 10.0 | 10.0 |
| 33 | PCC-1189 | .0613 | 3 AE/A | 10.0 | 0.0 | 0.0 | 10.0 | 30.0 |
| 33 | LI136 | 2 | V/V | 10.0 | 0.0 | 0.0 | 10.0 | 30.0 |
| 34 | PCC-1189 | .1225 | 3 AE/A V/V | 30.0 | 20.0 | 20.0 | 30.0 | 20.0 |
| 34 | L1136 | 2 | | 30.0 | 20.0 | 20.0 | 30.0 | 20.0 |
| 35 | PCC-1189 | 0.245 | 3 AE/A | 30.0 | 10.0 | 10.0 | 30.0 | 40.0 |
| 35 | L1136 | 2 | V/V | 30.0 | 10.0 | 10.0 | 30.0 | 40.0 |

-continued

Data for Example 10 (Two Week)

| | Herbicide | Rate | Unit | Corn | Tame Oat | Wheat | Pinto Bean | Sunflower |
|---|---|---|---|---|---|---|---|---|
| 36 | PCC-1189 | 0.49 | 3 AE/A | 10.0 | 0.0 | 0.0 | 20.0 | 70.0 |
| 36 | L1136 | 2 | V/V | 10.0 | 0.0 | 0.0 | 20.0 | 70.0 |
| 37 | Untreated | | | 0.0 | 0.0 | 0.0 | 0.0 | 0.0 |

Following are still other examples of herbicide compositions containing herbicide compound in acid form, that can be used according to the present description in combination with an acidifying agent. The first is a wettable powder and the second and third are microemulsion-forming concentrates.

| pcc1209 quizalofop-p, 80% - Wettable Powder | |
|---|---|
| 90% Quizalofop-p Acid | 88.8% |
| Morwet EFW, wetter, sulfonate | 1.5 |
| Polfon H, lignin, dispersant | 2.0 |
| Morwest D425, dispersant, urea-form condensate | 2.0 |
| Wessalon 50S, grinding aid, silica | 1.0 |
| Kaolin Clay, diluent | 4.7 |
| UHS 3 way acid mix MFC | |
| Surfonic L12-6, alcohol ethoxylate | 64.9 |
| Surfonic PE-1218, phosphate ester | 8.0 |
| 2,4D acid | 17.8 |
| MCPA acid | 7.6 |
| Dicamba acid | 1.6 |
| SAG 10, antifoam | 0.1 |
| pcc 1154, 1 lb/gal each 2,4D Acid, Fluroxypyr Acid MFC | |
| Tomadol 1-5, alcohol ethoxylate | 13.9 |
| Tomadol 1-7, alcohol ethoxylate | 13.9 |
| Surfonic T-15, tallow amine | 49.9 |
| Fluroxypyr acid | 11.1 |
| 2,4D acid | 11.1 |
| SAG 10 Antifoam | 0.1 |

We claim:

1. A method of controlling plant growth, the method comprising:
   preparing a herbicide composition, by:
      providing a herbicide concentrate composition comprising a herbicide compound in its charge neutral acid form; and
      combining the herbicide concentrate composition with acidifying agent and water to form a herbicide application composition having a pH below the pKa of the herbicide compound in acid form, wherein the pKa of the herbicide compound is below 6; and
   applying the herbicide application composition to a plant to control plant growth by the herbicide compound, wherein the herbicide compound damages and penetrates the plant surface and wherein the herbicide compound is dicamba acid (3,6-dichloro-O-anisic acid).

2. The method of claim 1 comprising:
   providing the herbicide concentrate composition,
   adding acidifying agent to the herbicide concentrate composition, and
   adding water to the herbicide concentrate composition.

3. The method of claim 2 wherein the herbicide concentrate composition is selected from the group consisting of: a microemulsion-forming concentrate, a microemulsion, and a suspension concentrate.

4. The method of claim 1 comprising combining the herbicide concentrate composition with water and acidifying agent in a spray tank to form the herbicide application composition.

5. The method of claim 1 wherein the herbicide concentrate composition is selected from the group consisting of: a microemulsion-forming concentrate, a microemulsion, and a suspension concentrate.

6. The method of claim 1 wherein the pKa of the herbicide compound is below 5.

7. The method of claim 1 wherein the acidifying agent is sulfuric acid.

8. The method of claim 1 wherein the acidifying agent is selected from the group consisting of: hydrochloric acid, nitric acid, acetic acid, phosphoric acid, polyphosphoric acid, perchloric acid, and combinations thereof, and the herbicide composition does not include sulfuric acid.

9. The method of claim 1 wherein the acidifying agent is selected from the group consisting of: sulfuric acid, hydrochloric acid, nitric acid, acetic acid, phosphoric acid, perchloric acid, polyphosphoric acid, and combinations thereof.

10. The method of claim 1 wherein the acidifying agent is selected from the group consisting of: sulfuric acid, hydrochloric acid, nitric acid, acetic acid, phosphoric acid, perchloric acid, and polyphosphoric acid, and the composition does not include a sulfuric acid adduct of the formula:

$$\begin{array}{c} R_1 \\ \phantom{R}\diagdown \\ \phantom{RR}N \\ \phantom{R}\diagup \\ R_2 \end{array} \!\!-\!\! \begin{array}{c} X \\ \| \\ C \\ \phantom{X} \end{array} \!\!-\!\! R_3$$

wherein X is chalcogen, and each of $R_1$, $R_2$, and $R_3$ is independently selected from hydrogen and organic radicals.

11. The method of claim 1 wherein the herbicide application composition does not include glyphosate acid.

12. The method of claim 1 wherein the herbicide concentrate composition contains essentially no organic solvent.

13. The method of claim 1 wherein the step of applying, the herbicide application composition is applied to control the growth of bushes, scrub brush, vines, or weeds.

* * * * *